(12) United States Patent
Minto et al.

(10) Patent No.: US 9,376,462 B2
(45) Date of Patent: Jun. 28, 2016

(54) **PROCESS FOR PREPARING DELTA-7,9(11) STEROIDS FROM *GANODERMA LUCIDUM* AND ANALOGS THEREOF**

(75) Inventors: Robert Minto, Indianapolis, IN (US); Erin Kennedy, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 426 days.

(21) Appl. No.: 13/876,971

(22) PCT Filed: Sep. 29, 2011

(86) PCT No.: PCT/US2011/053984
§ 371 (c)(1),
(2), (4) Date: Mar. 29, 2013

(87) PCT Pub. No.: WO2012/044817
PCT Pub. Date: Apr. 5, 2012

(65) Prior Publication Data
US 2013/0184244 A1    Jul. 18, 2013

Related U.S. Application Data

(60) Provisional application No. 61/388,910, filed on Oct. 1, 2010.

(51) Int. Cl.
C07J 9/00 (2006.01)
C07J 17/00 (2006.01)
C07J 71/00 (2006.01)
C07J 21/00 (2006.01)

(52) U.S. Cl.
CPC .. C07J 9/00 (2013.01); C07J 9/005 (2013.01); C07J 17/00 (2013.01); C07J 71/001 (2013.01); C07J 21/006 (2013.01)

(58) Field of Classification Search
USPC ........................................................ 552/547
See application file for complete search history.

(56) References Cited

U.S. PATENT DOCUMENTS

| 5,716,777 A | 2/1998 | Byskov et al. |
| 6,884,796 B2 | 4/2005 | Faarup et al. |
| 2002/0019376 A1 | 2/2002 | Savage et al. |
| 2008/0318870 A1 | 12/2008 | Moriarty et al. |

FOREIGN PATENT DOCUMENTS

WO    WO 00/68245    * 11/2000

OTHER PUBLICATIONS

International Search Report and Written Opinions established in connection with PCT/US2011/053984 and completed by the U.S. Searching Authority on Feb. 2, 2012.
Anaya at al. Allelochemical Potential of Metopium brownei. Journal of Chemical Ecology, 1999, vol. 25, No. 1, pp. 141-156; p. 147. Fig-4.
Dimir. Tetramethyldiamidophosphoric acid chloride mediated epoxide-diene conversion and steroidal aromatization.Tetrahedron. 2001, vol. 57. pp. 227-233; p. 228, table 1 h.
Gao at al. New Triterpene Aldehydes, Lucialdehydes A-C, from Ganoderma lucidum and Their Cytotoxicity against Murine and Human Tumor Cells. Chem. Pharm. Bull., 2002, vol. 50(6), pp. 837-840; title, pp. 838.
Julio Romero-Noguera, et al. "An Approach to the Study of the Fungal Deterioration of a Classical Art Material: Mastic Varnish". Electronic Journal of Biotechnology ISSN: 0717-3458, http://www.ejbiotechnology.info, DOI: 10.2225/vol. 13, issue 6, 2010.
Paryzek at al. Tetracyclic triterpenes. x. Solvent effect in reactions of tetrasubstituted triterpenoidal olefins with ozone. An allylic oxidation. Can. J. Chem., 1988, vol. 66, p. 2131. compounds 7 and 8.
Zhang at al. Tumor Cell Apoptosis Inducer from Ganoderma lucidum. Acta Edulis Fungi, 2006, vol. 13(2), pp. 23-28; p. 26, In 9; p. 24, In 11-24.

* cited by examiner

*Primary Examiner* — Barbara P Badio
(74) *Attorney, Agent, or Firm* — Barnes & Thornburg LLP

(57)    ABSTRACT

Processes for preparing lanostane triterpenes from the medicinal mushroom *Ganoderma lucidum*, and related compounds are described. Compounds, compositions, and methods for treating cancer are also described.

1 Claim, 4 Drawing Sheets

C

D

US 9,376,462 B2

PROCESS FOR PREPARING DELTA-7,9(11) STEROIDS FROM *GANODERMA LUCIDUM* AND ANALOGS THEREOF

CROSS REFERENCE TO RELATED APPLICATIONS

This application is a U.S. national counterpart application filed under 35 U.S.C. §371 of international application serial No. PCT/US2011/053984 filed Sep. 29, 2011, which claims priority to U.S. Provisional Patent Application No. 61/388,910 filed Oct. 1, 2010. The entire disclosures of PCT/US2011/053984 and U.S. Ser. No. 61/388,910 are hereby incorporated by reference.

TECHNICAL FIELD

The invention described herein pertains to processes for the preparation of delta7,9(11) steroids from *Ganoderma lucidum*, and related compounds and use of the compounds described herein to treat cancer.

BACKGROUND AND SUMMARY OF THE INVENTION

*Ganoderma lucidum* (Japanese name: Reishi) is widely used in Chinese traditional medicine as a dietary supplement. Ethnopharmacological studies of this ancient medicinal mushroom have shown that the triterpene extract and its components possess antiandrogenic,[1] anticomplement,[2] antihistamine,[3] anti-inflammatory,[4] antinociceptive,[5] antioxidant[6] and hypocholestremic[7] properties and inhibits the growth and proliferation of cancer cells.[8]

For example, Hattori and coworkers examined the inhibition of human immunodeficiency virus (HIV) by a range of fungal natural products. A methanol extract of the fruiting bodies of *Ganoderma lucidum* was reported to show moderate inhibitory effects against HIV-1 and its protease.[10a] In a primary screen for anti-HIV activity, ganodermanontriol (1) and ganoderiol F inhibited HIV-1-induced cytopathic effect in MT-4 cells; the activity was specific to the Δ7,9(11)-lanostadienes.[10a] A subsequent study was reported to show that ganoderic acid β, lucidumol B, ganodermanodiol, and ganodermanontriol appear to have significant inhibitory activity against recombinant HIV-1 protease and that the hydroxyl groups at C-23 or C-24 and C-25 may be essential for strong HIV-1 protease activity.[10b] Ganodermanontriol, as well as other triterpene alcohols, had significant anticomplement activity against the classical pathway (CP) of the complement system with IC(50) values of 17.2 μM.[2] The potency of triterpene alcohols in inhibiting CP activity reportedly improves when the number of side-chain hydroxymethyl groups increased.

*G. lucidum* triterpenes also inhibit the invasive behavior and proliferation of breast and prostate cancer cells through the down-regulation of cyclin-D1 expression and suppression of urokinase plasminogen activator (UPA) secretion.[11] It has been discovered herein that *G. lucidum* triterpene extract reduces proliferation of estrogen-dependent (MCF-7), and estrogen-independent (MDA-MB-231) breast cancer cells, possibly by the modulation of the estrogen receptor and NF-κB signaling.[8b] They inhibit growth, induce apoptosis, and suppress angiogenesis of breast, prostate, hepatoma, and colon cancer cells through a variety of mechanisms including the upregulation of p21 and Bax expression, suppression of protein kinase C, activation of caspase-3, and inhibition of secretion of vascular endothelial growth factor (VEGF) and transforming growth factor-1 (TGF-1), respectively.[11] Ganodermanontriol suppressed proliferation of human colon cancer cells in vitro and inhibited tumor growth in a xenograft model of colon cancer in vivo.[10c]

Over 150 highly oxygenated triterpenes have been reported from *G. lucidum*, however purification of novel steroids from the fruiting bodies of *G. lucidum* is reportedly unreliable due to variability of the natural product composition resulting from environmental and geographic factors, age, and handling. In addition, the content of the terpenoid acids and alcohols in *G. lucidum* tissue and spores has been shown by HPLC with UV detection to fluctuate widely depending on the growth substrate.[9] In addition, evaluation of the health effects of *Ganoderma* triterpene products that are widely used for alternative health care are confounded by the lack of standardization and characterization of the extracts. Ganodermanontriol (1, Scheme 1) is typically the dominant bioactive alcohol in *Ganoderma* extracts.[9] Accordingly, a need exists for a synthetic process for preparing *Ganoderma* alcohols, and related compounds for detailed evaluation.

In one illustrative embodiment of the invention, described herein is a method for preparation of ganodermanontriol. In another embodiment, described herein is a method for preparation of the stereoisomeric triols of ganodermanontriol. In another embodiment, described herein is a method for preparation of the various analogs of ganodermanontriol, including higher and lower homologs, alternative substituents, including halo and amino groups, and the like. In another embodiment, described herein are methods for treating cancer.

DETAILED DESCRIPTION

Figure 1:
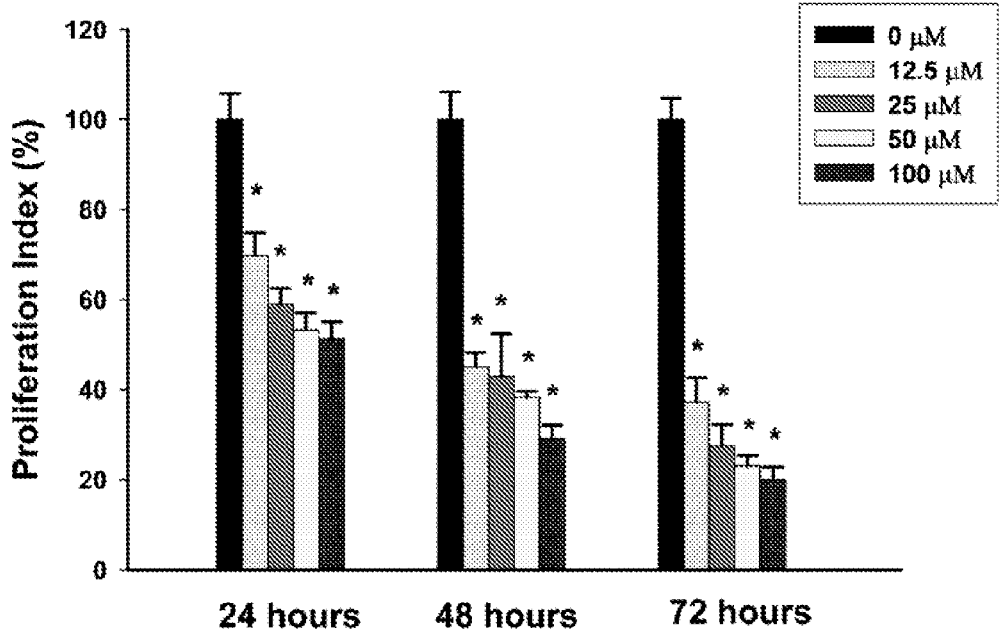
FIG. 1. The effect of *Ganoderma* triterpenes on proliferation of MCF7 cells. MCF7 cells are treated with: Panel (A) ganodermanontriol (compound 1) (0-100 μM), IC$_{50}$ at 72 h=5.8 μM; Panel (B) compound 13 (0-100 μM), IC$_{50}$ at 72 h=24.1 μM; Panel (C) compound 14 (0-100 μM), IC$_{50}$ at 72 h=16.3 μM; and Panel (D) compound 15 (0-100 μM), IC$_{50}$ at 72 h=24.1 μM. Cell proliferation is determined by the tetrazolium salt method. Data are the means±SD of triplicate determinations. Similar results are obtained in at least two additional experiments. *p<0.05.
Figure 1:
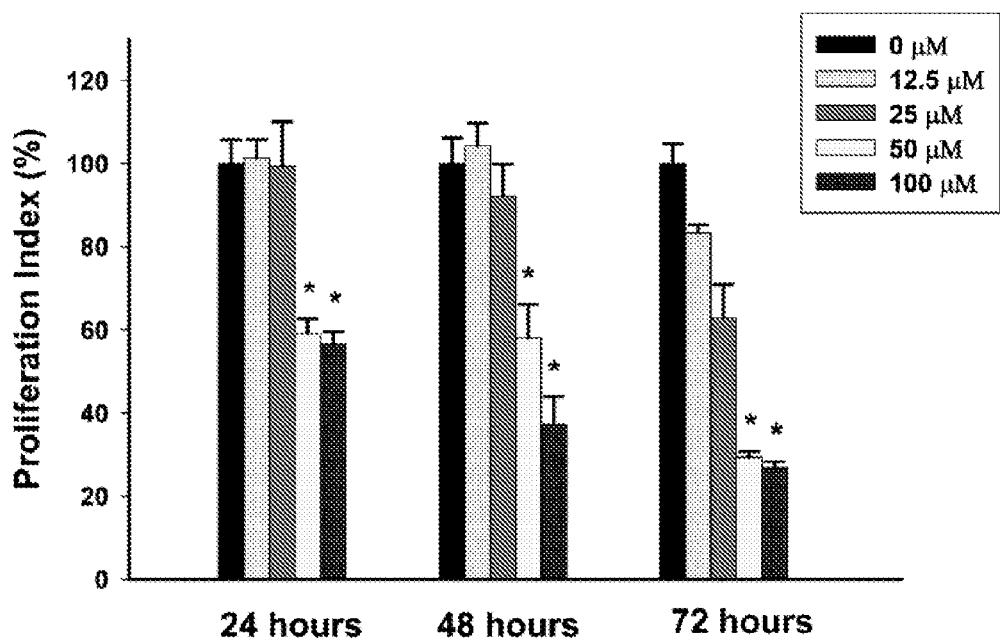
Figure 1:
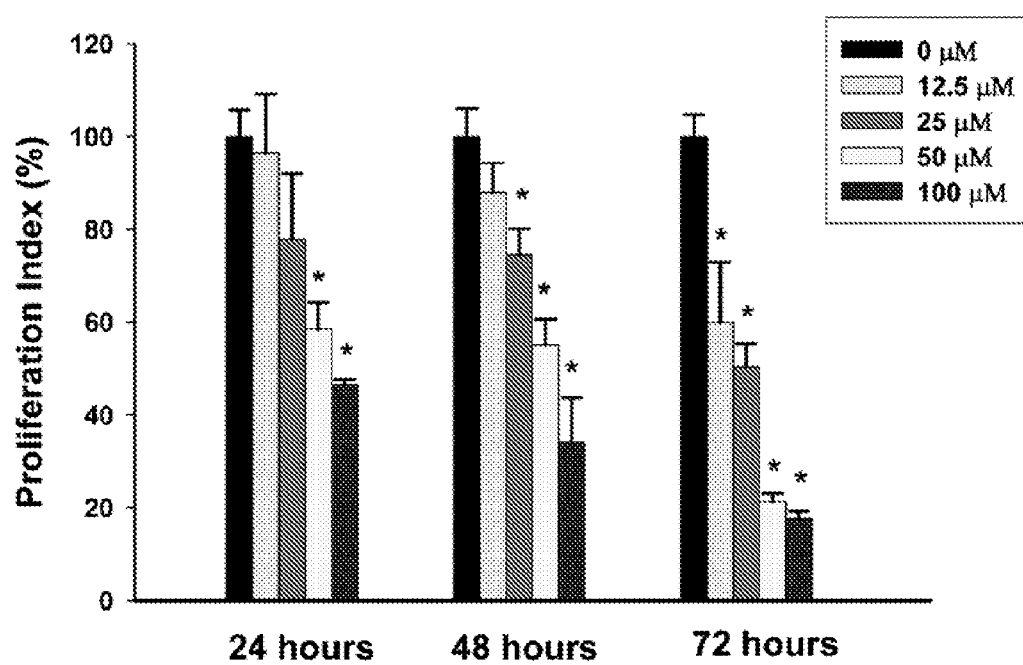
Figure 1:
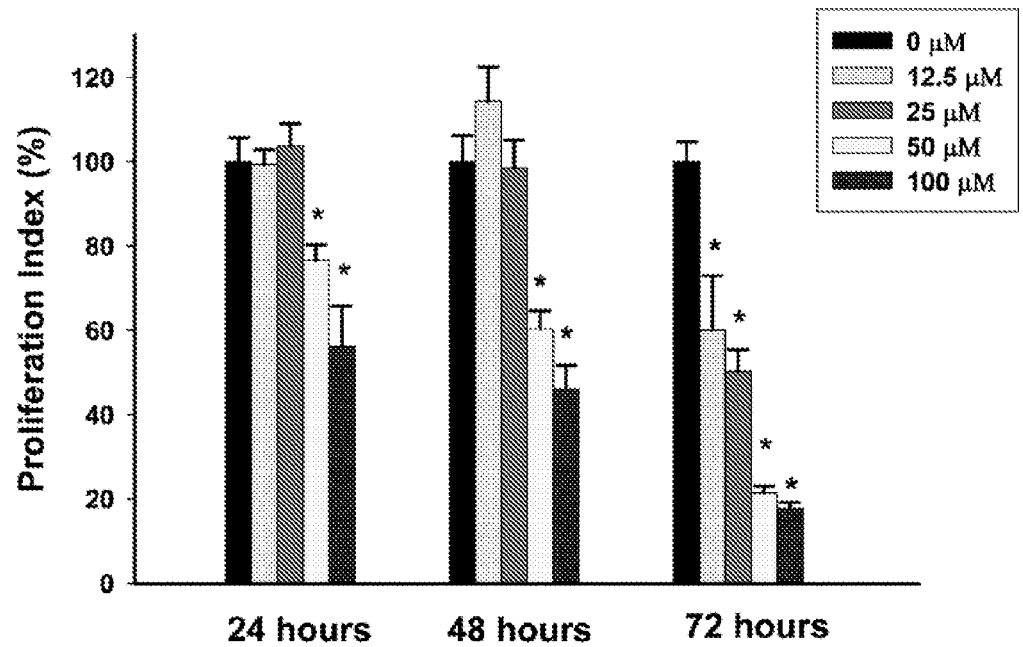

In one embodiment, described herein is a compound of the formula [[this should be the broadest scope, then step down to the following listing specific substituents as amended in the claims, then after that step down to the novel compounds]]

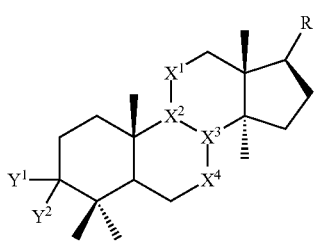

or a pharmaceutically acceptable salt thereof, wherein: R is a substituted alkyl, alkenyl, or alkynyl, providing that at least one substituent is an oxygen containing functional group; $X^1$ and $X^4$ are each independently selected from the group consisting of CH, substituted CH, and $CH_2$; $X^2$ and $X^3$ are each independently selected from the group consisting of C, substituted C, and CH; and $Y^1$ and $Y^2$ are each independently selected from the group consisting of hydrogen, halo, hydroxy, derivatives of hydroxy, optionally substituted alkyl, optionally substituted alkenyl, optionally substituted alkynyl, optionally substituted arylalkyl, and optionally substituted heteroarylalkyl; or $Y^1$ and $Y^2$ are taken together to form a carbonyl or derivative thereof; providing that the compound is not ganodermanontriol.

In another embodiment, R is substituted with one or more halogens.

In another embodiment, described herein is a compound as described above wherein the oxygen containing functional group is selected from the group consisting of hydroxy, epoxy, carbonyl, carboxylic acid, and derivatives of each of the foregoing.

In another embodiment, described herein is a compound as described above wherein R is alkenyl.

In another embodiment, described herein is a compound as described above wherein R is an aldehyde.

In another embodiment, described herein is a compound as described above wherein R is an alpha/beta unsaturated carboxylic acid or derivative thereof.

In another embodiment, described herein is a compound as described above wherein R is hydroxyalkenyl.

In another embodiment, described herein is a compound as described above wherein R is polyhydroxyalkyl.

In another embodiment, described herein is a compound as described above wherein $X^1$ and $X^2$ are taken together to form CH=C.

In another embodiment, described herein is a compound as described above wherein $X^2$ and $X^3$ are taken together to form CH=C.

In another embodiment, described herein is a compound as described above wherein $X^3$ and $X^4$ are taken together to form CH=C.

In another embodiment, described herein is a compound as described above wherein $X^1$ and $X^2$ are taken together to form an epoxide.

In another embodiment, described herein is a compound as described above wherein $X^2$ and $X^3$ are taken together to form an epoxide.

In another embodiment, described herein is a compound as described above wherein $X^3$ and $X^4$ are taken together to form an epoxide.

In another embodiment, described herein is a compound as described above wherein $Y^1$ and $Y^2$ are taken together to form a ketal.

In another embodiment, described herein is a compound as described above wherein $Y^1$ and $Y^2$ are taken together to form a cyclic ketal.

In another embodiment, described herein is a pharmaceutical composition comprising a compound as described above and one or more carriers, diluents, or excipients, or a combination thereof.

In another embodiment, described herein is a method for treating a cancer in a patient, the method comprising the step of administering to the patient a therapeutically effective amount of a compound or composition as described above.

In another embodiment, described herein is a method as described above wherein the therapeutically effective amount inhibits cancer cell proliferation.

In another embodiment, described herein is a method as described above wherein the therapeutically effective amount inhibits cancer cell invasion.

In another embodiment, described herein is a method as described above wherein the therapeutically effective amount inhibits cancer cell metathesis.

In another embodiment, described herein is a method as described above wherein the cancer is breast cancer.

In another embodiment, described herein is a method as described above wherein the therapeutically effective amount inhibits breast to lung cancer cell metathesis.

In another embodiment, described herein is a method as described above wherein the cancer is prostate cancer.

In another embodiment, described herein is a method as described above wherein the cancer is a gastric or gastrointestinal cancer.

In another embodiment, described herein is a method for treating a disease in a patient, where the disease is responsive to an antiandrogenic, anticomplement, antihistamine, anti inflammatory, antinociceptive, antioxidant, or hypocholestremic activity, the method comprising the step of administering to the patient a therapeutically effective amount of a compound or composition as described above.

In another embodiment, described herein is a process for preparing ganodermanontriol or an analog or derivative thereof, the process comprising one or more of the following steps:

(a)

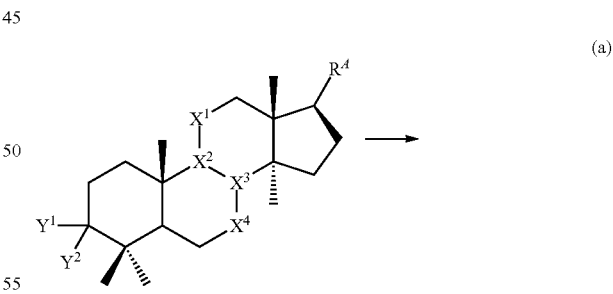

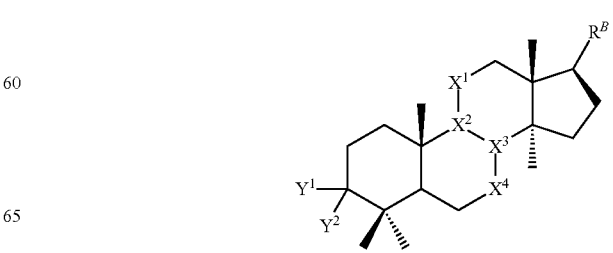

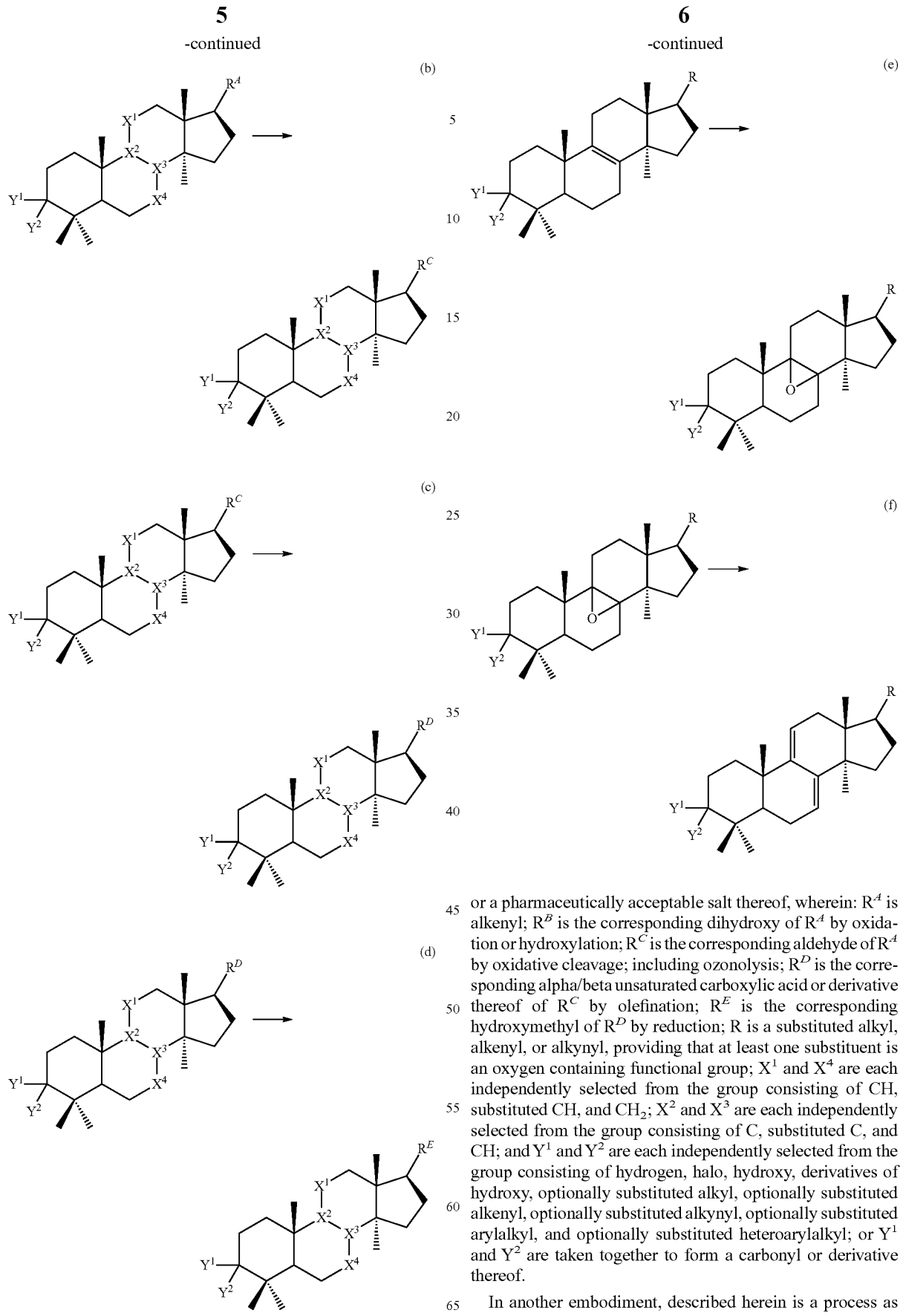

or a pharmaceutically acceptable salt thereof, wherein: $R^A$ is alkenyl; $R^B$ is the corresponding dihydroxy of $R^A$ by oxidation or hydroxylation; $R^C$ is the corresponding aldehyde of $R^A$ by oxidative cleavage; including ozonolysis; $R^D$ is the corresponding alpha/beta unsaturated carboxylic acid or derivative thereof of $R^C$ by olefination; $R^E$ is the corresponding hydroxymethyl of $R^D$ by reduction; R is a substituted alkyl, alkenyl, or alkynyl, providing that at least one substituent is an oxygen containing functional group; $X^1$ and $X^4$ are each independently selected from the group consisting of CH, substituted CH, and $CH_2$; $X^2$ and $X^3$ are each independently selected from the group consisting of C, substituted C, and CH; and $Y^1$ and $Y^2$ are each independently selected from the group consisting of hydrogen, halo, hydroxy, derivatives of hydroxy, optionally substituted alkyl, optionally substituted alkenyl, optionally substituted alkynyl, optionally substituted arylalkyl, and optionally substituted heteroarylalkyl; or $Y^1$ and $Y^2$ are taken together to form a carbonyl or derivative thereof.

In another embodiment, described herein is a process as described above where the analog or derivative of ganodermanontriol is a compound of any of the above formulae.

Additional illustrative embodiments are described in the following enumerated clauses:
1. A process for preparing a compound of formula (I)
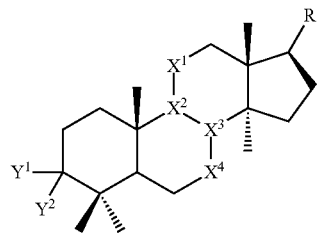
(I)
or a pharmaceutically acceptable salt thereof; the process comprising one or more of the steps:
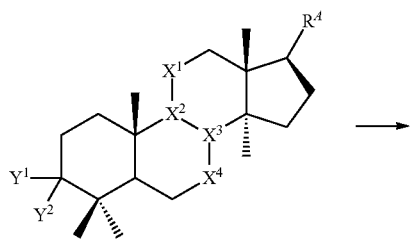
(a)
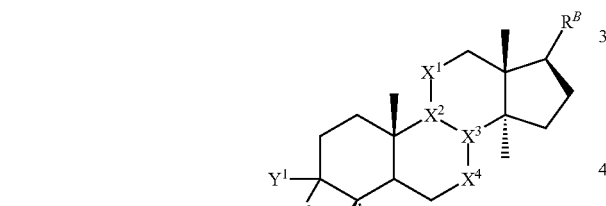
(b)
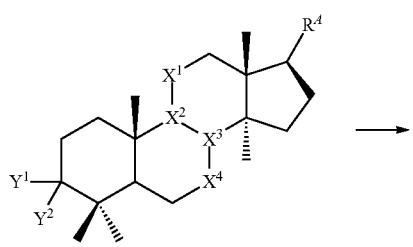
(c)
-continued
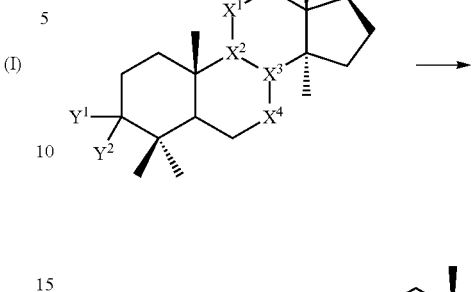
(c)
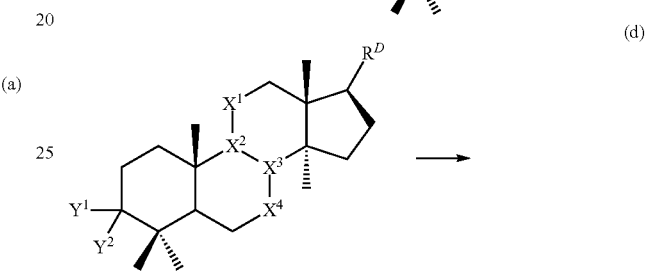
(d)
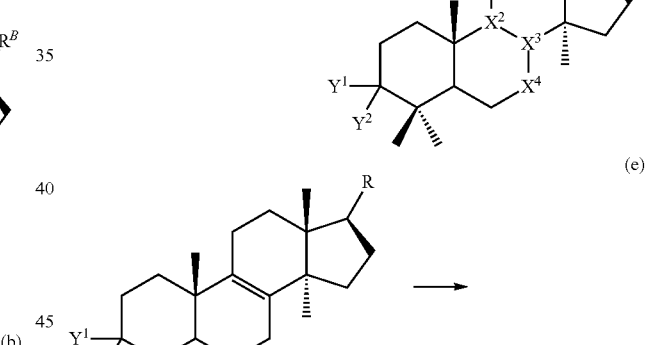
(e)
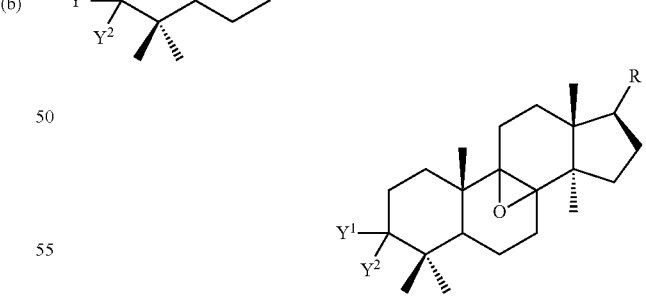
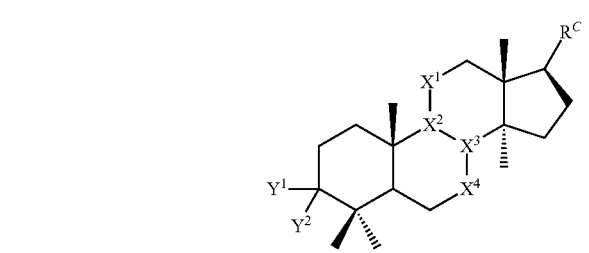
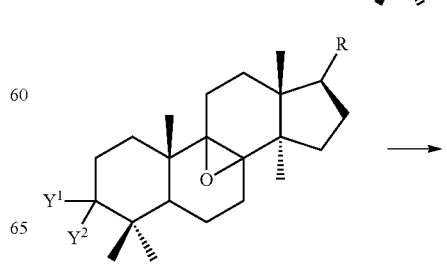
(f)

9

-continued

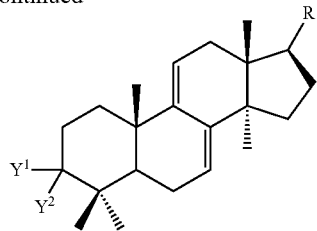

wherein:

$R^A$ is alkenyl;

$R^B$ is the corresponding dihydroxy derivative of $R^A$, which may be illustratively prepared by oxidation or hydroxylation;

$R^C$ is the corresponding aldehyde derivative of $R^A$, which may be illustratively prepared by oxidative cleavage;

$R^D$ is the corresponding alpha/beta unsaturated carboxylic acid or derivative thereof of $R^C$, which may be illustratively prepared by olefination;

$R^E$ is the corresponding hydroxymethyl derivative of $R^D$, which may be illustratively prepared by reduction;

R is an optionally substituted alkyl, alkenyl, or alkynyl, where said substituents are independently selected from the group consisting of oxygen containing functional groups, halo, amino and derivatives thereof, optionally substituted aryl, and optionally substituted heteroaryl, and combinations thereof;

$X^1$ and $X^4$ are each independently selected from the group consisting of CH, substituted CH, and $CH_2$;

$X^2$ and $X^3$ are each independently selected from the group consisting of C, substituted C, and CH; and $Y^1$ and $Y^2$ are each independently selected from the group consisting of hydrogen, halo, hydroxy, derivatives of hydroxy, optionally substituted alkyl, optionally substituted alkenyl, optionally substituted alkynyl, optionally substituted arylalkyl, and optionally substituted heteroarylalkyl; or $Y^1$ and $Y^2$ are taken together to form a carbonyl or derivative thereof.

2. The process of clause 1 wherein step (b) is performed by oxidative cleavage in the presence of ozone.

3. The process of clause 1 or 2 wherein the oxygen containing functional group is selected from the group consisting of hydroxy, epoxy, carbonyl, carboxylic acid, and derivatives of each of the foregoing.

4. The process of any one of the preceding clauses wherein R is alkenyl.

5. The process of any one of the preceding clauses wherein R is an aldehyde.

6. The process any one of the preceding clauses wherein R is an alpha/beta unsaturated carboxylic acid or derivative thereof.

7. The process any one of the preceding clauses wherein R is hydroxyalkenyl.

8. The process of any one of the preceding clauses wherein R is polyhydroxyalkyl.

9. The process of any one of the preceding clauses wherein $X^1$ and $X^2$ are taken together to form CH=C.

10. The process of any one of the preceding clauses wherein $X^2$ and $X^3$ are taken together to form C=C.

11. The process of any one of the preceding clauses wherein $X^3$ and $X^4$ are taken together to form C=CH 12. The process of any one of the preceding clauses wherein $X^1$ and $X^2$ are taken together to form an epoxide.

13. The process of any one of the preceding clauses wherein $X^2$ and $X^3$ are taken together to form an epoxide.

10

14. The process of any one of the preceding clauses wherein $X^3$ and $X^4$ are taken together to form an epoxide.

15. The process of any one of the preceding clauses wherein $Y^1$ and $Y^2$ are taken together to form a ketal.

16. The process of any one of the preceding clauses wherein $Y^1$ and $Y^2$ are taken together to form a cyclic ketal.

17. The process of any one of the preceding clauses wherein R is optionally substituted aminoalkenyl.

18. The process of any one of the preceding clauses wherein R is optionally substituted aminoalkyl.

19. The process of any one of the preceding clauses wherein R is optionally substituted haloalkenyl.

20. The process of any one of the preceding clauses wherein R is optionally substituted haloalkyl.

21. The process of any one of the preceding clauses wherein the compound is ganodermanontriol, or a stereoisomer thereof.

22. The process of any one of the preceding clauses wherein the compound is ganodermanontriol.

23. A compound of the formula

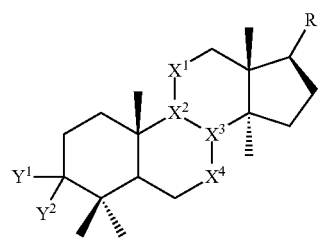

or a pharmaceutically acceptable salt thereof, wherein:

R is an optionally substituted alkyl, alkenyl, or alkynyl, where said substituents are independently selected from the group consisting of oxygen containing functional groups, halo, amino and derivatives thereof, optionally substituted aryl, and optionally substituted heteroaryl, and combinations thereof;

$X^1$ and $X^4$ are each independently selected from the group consisting of CH, and $CH_2$;

$X^2$ and $X^3$ are each independently selected from the group consisting of C, substituted C, and CH; and $Y^1$ and $Y^2$ are each independently selected from the group consisting of hydrogen, halo, hydroxy, derivatives of hydroxy, optionally substituted alkyl, optionally substituted alkenyl, optionally substituted alkynyl, optionally substituted arylalkyl, and optionally substituted heteroarylalkyl; or $Y^1$ and $Y^2$ are taken together to form a carbonyl or derivative thereof;

wherein the compound is not of the formula selected from the group consisting of

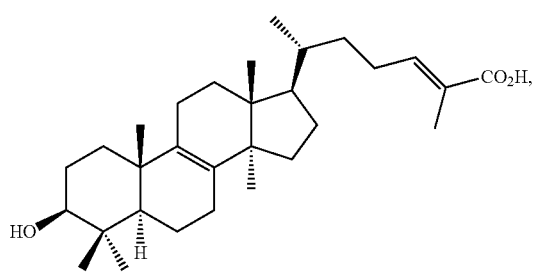

11
-continued
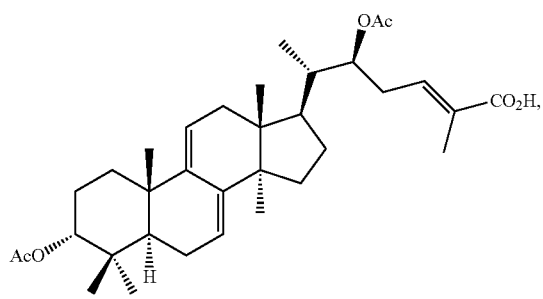
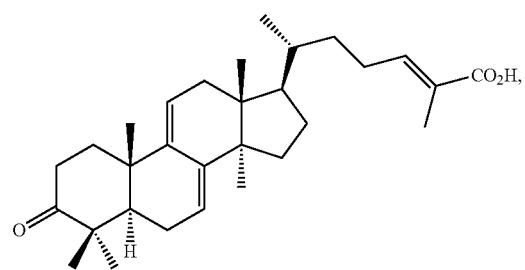
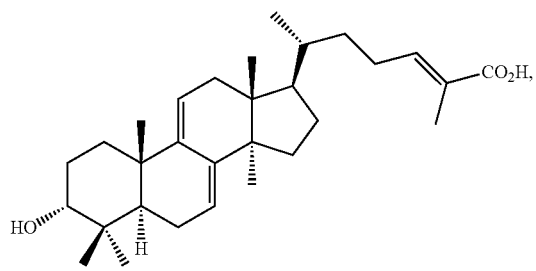
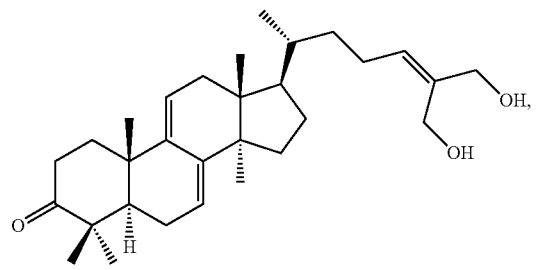
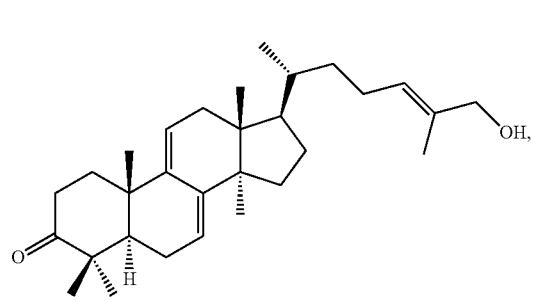
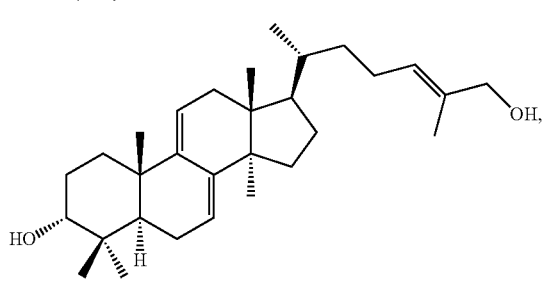
12
-continued
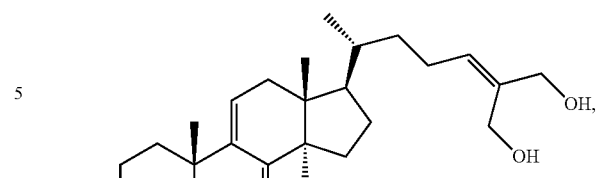
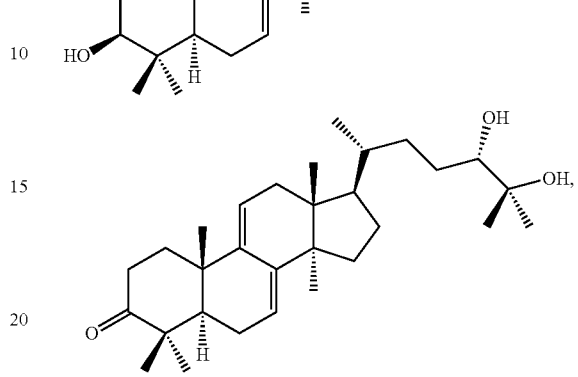
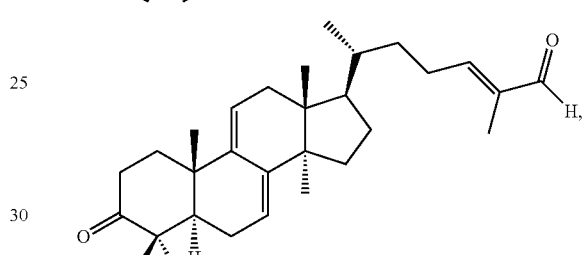
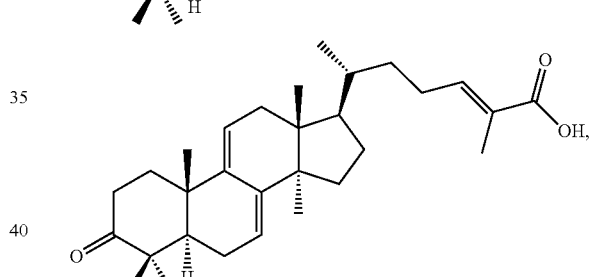
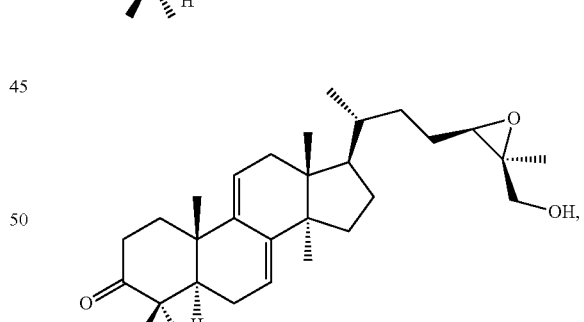
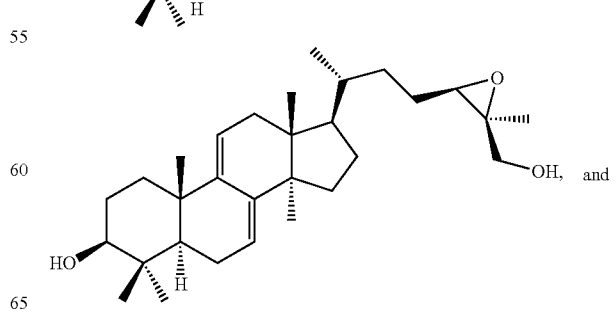
and -continued

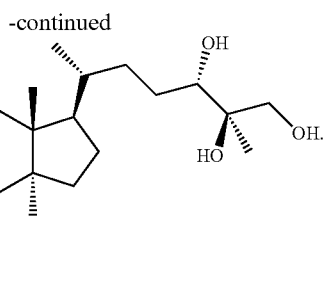

24. The compound of clause 23 wherein the oxygen containing functional group is selected from the group consisting of hydroxy, epoxy, carbonyl, carboxylic acid, and derivatives of each of the foregoing.

25. The compound of clause 23 or 24 wherein R is alkenyl.

26. The compound of any one of the preceding clauses wherein R is an aldehyde.

27. The compound of any one of the preceding clauses wherein R is an alpha/beta unsaturated carboxylic acid or derivative thereof.

28. The compound of any one of the preceding clauses wherein R is hydroxyalkenyl.

29. The compound of any one of the preceding clauses wherein R is polyhydroxyalkyl.

30. The compound of any one of the preceding clauses wherein R is optionally substituted aminoalkenyl.

31. The compound of any one of the preceding clauses wherein R is optionally substituted aminoalkyl.

32. The compound of any one of the preceding clauses wherein R is optionally substituted haloalkenyl.

33. The compound of any one of the preceding clauses wherein R is optionally substituted haloalkyl.

34. The compound of any one of the preceding clauses wherein $X^1$ and $X^2$ are taken together to form CH=C.

35. The compound of any one of the preceding clauses wherein $X^2$ and $X^3$ are taken together to form C=C.

36. The compound of any one of the preceding clauses wherein $X^3$ and $X^4$ are taken together to form C=CH.

37. The compound of any one of the preceding clauses wherein $X^2$ and $X^3$ are taken together to form an epoxide.

38. The compound of any one of the preceding clauses wherein $Y^1$ and $Y^2$ are taken together to form a ketal.

39. The compound of any one of the preceding clauses wherein $Y^1$ and $Y^2$ are taken together to form a cyclic ketal.

40. A pharmaceutical composition comprising a compound of any one of clauses 19 to 39, and one or more carriers, diluents, or excipients, or a combination thereof.

41. A method for treating a cancer in an animal, the method comprising the step of administering to the animal a therapeutically effective amount of the compound of any one of clauses 23 to 39, or a pharmaceutical composition comprising the compound of any one of clauses 23 to 39, and one or more carriers, diluents, or excipients, or a combination thereof.

42. The method of clause 41 wherein the therapeutically effective amount inhibits cancer cell proliferation.

43. The method of clause 41 or 42 wherein the therapeutically effective amount inhibits cancer cell invasion.

44. The method of clause 41, 42, or 43 wherein the therapeutically effective amount inhibits cancer cell metathesis.

45 The method of any one of clauses 41 to 44 wherein the cancer is breast cancer.

46. The method of any one of clauses 41 to 45 wherein the therapeutically effective amount inhibits breast to lung cancer cell metathesis.

47. The method of any one of clauses 41 to 44 wherein the cancer is prostate cancer.

48. The method of any one of clauses 41 to 44 wherein the cancer is a gastric or gastrointestinal cancer.

49. A method for treating a disease in a patient, where the disease is responsive to an antiandrogenic, anticomplement, antihistamine, anti inflammatory, antinociceptive, antioxidant, or hypocholestremic activity, the method comprising the step of administering to the patient a therapeutically effective amount of a compound of any one of clauses 23 to 39.

50. Use of a therapeutically effective amount of the compound of any one of clauses 23 to 39, or a pharmaceutical composition comprising the compound of any one of clauses 23 to 39, and one or more carriers, diluents, or excipients, or a combination thereof, in the manufacture of a medicament for treating cancer.

51. A composition comprising the compound of any one of the preceding clauses for the treatment of cancer.

52. The process of clause 1 wherein the compound of formula (I) is the compound of any one of clauses 23 to 39.

53. A compound of formula

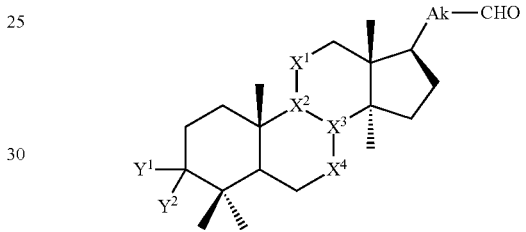

wherein Ak is alkyl, alkenyl, or alkynyl, each of which is optionally substituted;

$X^1$ and $X^4$ are each independently selected from the group consisting of CH, substituted CH, and $CH_2$;

$X^2$ and $X^3$ are each independently selected from the group consisting of C, substituted C, and CH; and $Y^1$ and $Y^2$ are each independently selected from the group consisting of hydrogen, halo, hydroxy, derivatives of hydroxy, optionally substituted alkyl, optionally substituted alkenyl, optionally substituted alkynyl, optionally substituted arylalkyl, and optionally substituted heteroarylalkyl; or $Y^1$ and $Y^2$ are taken together to form a carbonyl or derivative thereof.

54. A compound of the formula

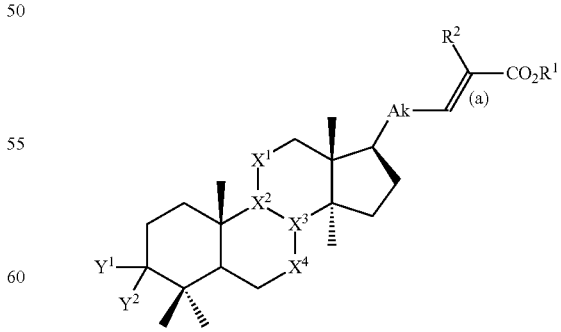

wherein Ak is alkyl, alkenyl, or alkynyl, each of which is optionally substituted;

the bond labeled (a) represents a Z-double bond, an E-double bond or a mixture of E- and Z-bonds;

$R^1$ is alkyl, alkenyl, or arylalkyl, each of which is optionally substituted;

$R^2$ is alkyl or alkenyl, each of which is optionally substituted;

$X^1$ and $X^4$ are each independently selected from the group consisting of CH, substituted CH, and $CH_2$;

$X^2$ and $X^3$ are each independently selected from the group consisting of C, substituted C, and CH; and $Y^1$ and $Y^2$ are each independently selected from the group consisting of hydrogen, halo, hydroxy, derivatives of hydroxy, optionally substituted alkyl, optionally substituted alkenyl, optionally substituted alkynyl, optionally substituted arylalkyl, and optionally substituted heteroarylalkyl; or $Y^1$ and $Y^2$ are taken together to form a carbonyl or derivative thereof.

55. A compound of the formula

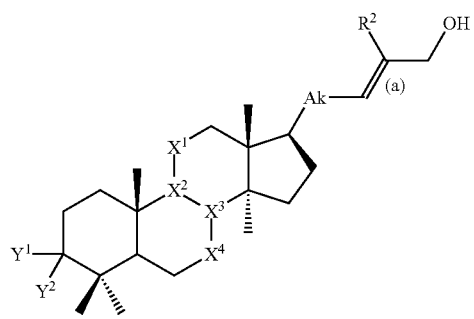

wherein Ak is alkyl, alkenyl, or alkynyl, each of which is optionally substituted;

the bond labeled (a) represents a Z-double bond, an E-double bond or a mixture of E- and Z-bonds;

$R^2$ is alkyl or alkenyl, each of which is optionally substituted;

$X^1$ and $X^4$ are each independently selected from the group consisting of CH, substituted CH, and $CH_2$;

$X^2$ and $X^3$ are each independently selected from the group consisting of C, substituted C, and CH; and $Y^1$ and $Y^2$ are each independently selected from the group consisting of hydrogen, halo, hydroxy, derivatives of hydroxy, optionally substituted alkyl, optionally substituted alkenyl, optionally substituted alkynyl, optionally substituted arylalkyl, and optionally substituted heteroarylalkyl; or $Y^1$ and $Y^2$ are taken together to form a carbonyl or derivative thereof.

56. A compound of the formula

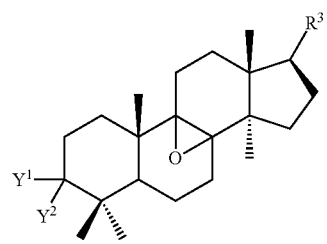

wherein $R^3$ is a substituted alkyl, alkenyl, or alkynyl, providing that at least one substituent is an oxygen containing functional group, a halo, or an amino and derivatives thereof; and $Y^1$ and $Y^2$ are each independently selected from the group consisting of hydrogen, halo, hydroxy, derivatives of hydroxy, optionally substituted alkyl, optionally substituted alkenyl, optionally substituted alkynyl, optionally substituted arylalkyl, and optionally substituted heteroarylalkyl; or $Y^1$ and $Y^2$ are taken together to form a carbonyl or derivative thereof.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures, unless otherwise indicated. In each of the foregoing and following embodiments, it is also to be understood that the formulae include and represent any and all crystalline forms, partially crystalline forms, and non crystalline and/or amorphous forms of the compounds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may additionally include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "aryl" includes monocyclic and polycyclic aromatic groups, including aromatic carbocyclic and aromatic heterocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. The term "hydroxy derivative" also includes carbamate, and the like.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein the term "oxygen containing functional group" includes carboxylate and derivatives thereof, carbonyl and derivatives thereof, and hydroxy and derivatives thereof, optionally substituted oxiranes, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

It is to be understood that the embodiments described herein may be combined in all possible chemically relevant ways.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidural, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

The following publications, and each additional publication cited herein, are incorporated herein by reference in their entirety.

1. (a) Liu, J.; Kurashiki, K.; Shimizu, K.; Kondo, R. Biol. Pharm. Bull., 2006, 29, 392. (b) Liu, J.; Kurashika, K.; Shimizu, K.; Kondo, R. Bioorg. Med. Chem. 2006, 14, 8654. (c) Liu, J.; Tamura, S.; Kurashiki, K.; Shimizu, K.; Noda, K.; Konishi, F.; Kumamoto, S.; Kondo, R. Chem. Biodiv. 2009, 6, 231.
2. Min, B. S.; J., G. J.; Hattori, M.; Lee, H. K.; Kim, Y. H. Planta Med. 2001, 67, 811-814.
3. Kohda, H.; Tokumoto, W.; Sakamoto, K.; Fujii, M.; Hirai, Y.; Yamasaki, K.; Komoda, Y.; Nakamura, H.; Ishihara, S.; Uchida, M. Chem Pharm Bull (Tokyo) 1985, 33, 1367.
4. Ko, H. H.; Hung, C. F.; Wang, J. P.; Lin, C. N. Phytochemistry 2008, 69, 234; (b) Dudhgaonkar, S.; Thyagarajan, A.; Sliva, D. Int. Immunopharmacol. 2009, 11, 1272-1280.
5. Koyama, K.; Imaizumi, T.; Akiba, M.; Kinoshita, K.; Takahashi, K.; Suzuki, A.; Yano, S.; Horie, S.; Watanabe, K.; Naoi, Y. Planta Med. 1997, 63, 224.
6. Zhu, M.; Chang, Q.; Wong, L. K.; Chong, F. S.; Li, R. C. Phytother. Res. 1999, 13, 529.
7. (a) Shiao, M. S. Chem. Rec. 2003, 3, 172. (b) Hajjaj, H.; Macé, C.; Roberts, M.; Niederberger, P.; Fay, L. B. Appl. Environ. Microbiol. 2005, 71, 3653; (c) Berger, A.; Rein, D.; Kratky, E.; Monnard, I.; Hajjaj, H.; Meirim, I.; Piguet-Welsch, C.; Hauser, J.; Mace, K.; Niederberger, P. Lipids Health Dis 2004, 3, 2.
8. (a) Jiang, J.; Slivova, V.; Sliva, D. Int. J. Oncol. 2006, 29, 695. (b) Jiang, J.; Grieb, B.; Thyagarajan, A.; Sliva, D. Int. J. Mol. Med. 2008, 21, 577-584. (c) Thyagarajan, A.; Jedinak, A.; Nguyen, H.; Terry, C.; Baldridge, L.; Jiang, J.; Sliva, D. Nutr. Cancer 2010, 62, 630-640 (d) Gao, J. J.; Min, B. S.; Ahn, E. M.; Nakamura, N.; Lee, H. K.; Hattori, M. Chem Pharm Bull (Tokyo) 2002, 50, 837.
9. Gao, J.-J.; Nakamura, N.; Min, B.-S.; Hirakawa, A.; Zuo, F.; Hattori, M. Chem. Pharm. Bull. 2004, 52, 688.
10. (a) El-Mekkawy, S.; Meselhy, M. R.; Nakamura, N.; Tezuka, Y.; Hattori, M.; Kakiuchi, N.; Shimotohno, K.; Kawahta, T.; Otake, T. Phytochemistry 1998, 49, 1651-1657. (b) Min, B. S.; Nakamura, N.; Miyashiro, H.; Bae, K. W.; Hattori, M. Chem. Pharm. Bull. 1998, 46, 1607-1612; (c) Jedinak, A.; Thyagarajan-Sahu, A.; Jiang, J.; Sliva, D. Int. J. Oncol. 2011, 38, 761-767.
11. Sliva, D. Leukemia Res. 2006, 30, 767-768.
12. Mancuso, A. J.; Huang, S.-L.; Swern, D. J. Org. Chem. 1978, 43, 2480.
13. (a) Solaja, B.; Dermanovic, M. J. Serb. Chem. Soc. 1993, 58, 275. (b) Solaja, B.; Dermanovic, M.; Lim, D.-M.; Paik, Y.-K.; Tinant, B.; Declerq, J.-P. Steroids 1997, 62, 709.
14. For an epoxide opening route with concentrated H2SO4 in refluxing acetic acid, see Brewis, S.; Halsall, T. G.; Sayer, G. C. J. Chem. Soc. 1962, 2763.
15. Paryzek, Z.; Martynow, J. Can. J. Chem. 1988, 66, 2130.
16. 15 (a) Franci, X.; Martina, S. L. X.; McGrady, J. E.; Webb, M. R.; Donald, C.; Taylor, R. J. K. Tetrahedron Lett. 2003, 44, 7735. (b) Ando, K. Tetrahedron Lett. 1995, 36, 4105. (c) Ando, K. J. Org. Chem. 1998, 63, 8411.
17. Touchard, F. P.; Capelle, N.; Mercier, M. Adv. Synth. Catal. 2005, 347, 707.
18. Chun, J.; Byun, H.-S.; Bittman, R. J. Org. Chem. 2002, 68, 348.
19. Gemma, S.; Gabellieri, E.; Sanna Coccone, S.; Marti, F.; Taglialatela-Scafati, O.; Novellino, E.; Campiani, G.; Butini, S. J. Org. Chem. 2010, 75, 2333.
20. Bach, R. D.; Canepa, C.; Winter, J. E.; Blanchette, P. E. J. Org. Chem. 1997, 62, 5191.
21. Kolb, H. C.; VanNieuwenhze, M. S.; Sharpless, K. B. Chem. Rev. 1994, 94, 2483.
22. Arisawa, M.; Fujita, A.; Hayashi, T.; Shimizu, M.; Morita, N.; Kikuchi, T.; Kadota, S.; Tezuka, Y. J. Nat. Prod. 1988, 51, 54-59.

23. (a) Okumura, K.; Nakamura, Y.; Takeuchi, S.; Kato, I.; Fujimoto, Y.; Ikekawa, N. Chem. Pharm. Bull. 2003, 51, 1177. (b) Kolb, H. C.; VanNieuwenhze, M. S.; Sharpless, K. B. Chem. Rev. 1994, 94, 2483.

24. (a) Xu, D.; Park, C. Y.; Sharpless, K. B. Tetrahedron Lett. 1994, 35, 2495; (b) Xu, D.; Crispino, G. A.; Sharpless, K. B. J. Am. Chem. Soc. 1992, 114, 7570.

ILLUSTRATIVE EXAMPLES

The following examples further illustrate specific embodiments of the invention. However, the following examples should not be interpreted in any way to limit the invention.

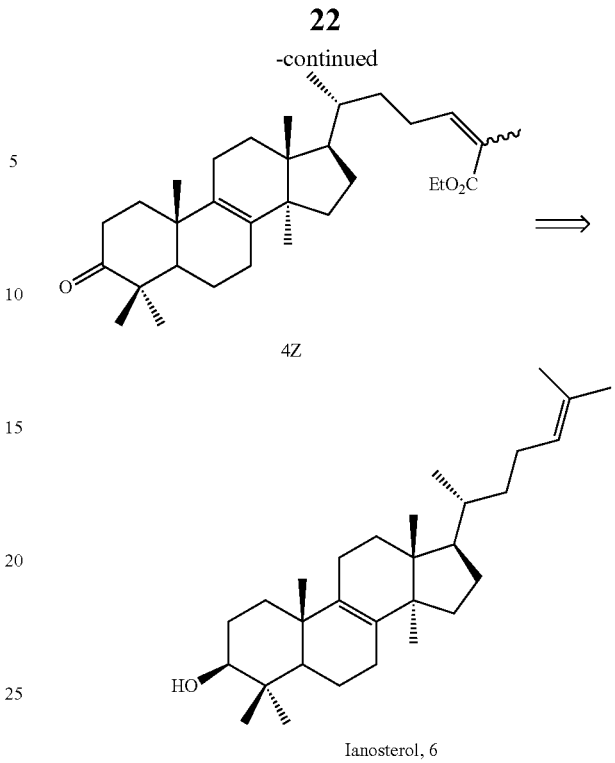

Retrosynthetically, the diene of the tetracyclic core was chosen to be installed first (Scheme 1). The starting material, lanosterol (6), was believed to be the most cost effective precursor containing the correct methyl branch configurations. However, it was ultimately found that side-chain revisions were optimally interwoven with diene core preparation through a 5-step sequence (Scheme 2). Ozonolysis attempts with 6 appeared to be ineffective, presumably due to poor solubility at low temperatures. As a result, 6 was pre-oxidized in order to increase the steroid's solubility. Swern oxidation[12] of lanosterol (56% pure) led to a mixture of 7 and dihydrolanosterone, which is derived from the main contaminant in commercial lanosterol. Exhaustive ozonolysis of 7 cleaved the side-chain and formed aldehyde 5, which could be easily purified from the 24,25-dihydrosteroid (Scheme 2).

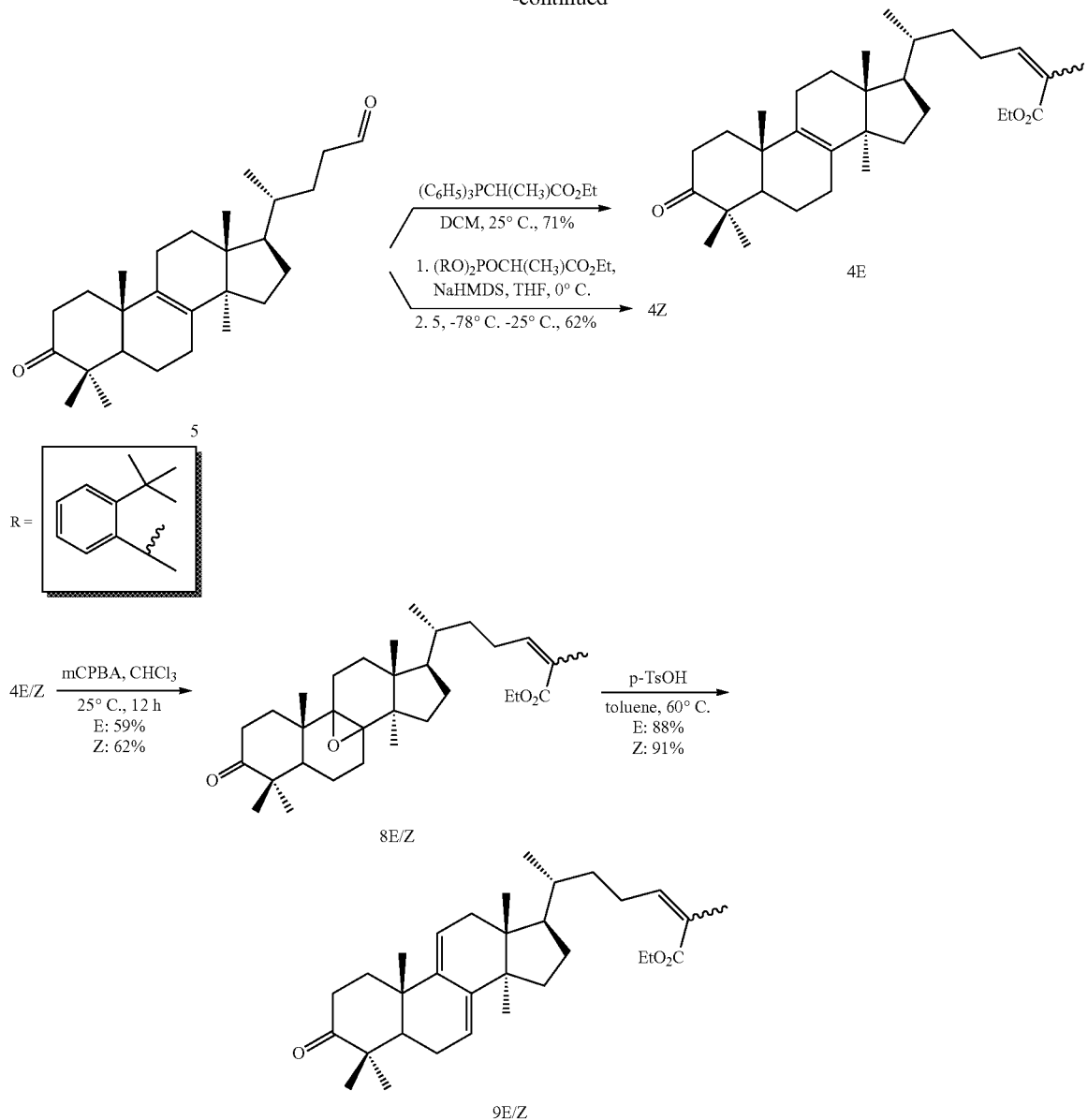

While other seemingly more arduous approaches exist,[13] a direct route to the Δ7,9(11)-diene core had been reported to proceed through the epoxide.[14] It has also been reported that the 8,9-epoxide can be formed by ozone treatment and converted to the diene in a solvent-dependent fashion; however, attempts to reproducibly effect this reaction appeared to fail.[15] Direct mCPBA epoxidation of 5, resulted in partial Baeyer-Villager oxidation at the aldehyde, leading to a 5:3:2 mixture of carboxylic acid, epoxide and 5.

Without being bound by theory, it was expected that the sterically protected, normally unreactive, tetrasubstituted 8,9-olefin would be more susceptible to reaction with peracids as it is believed to be more electron rich than the α,β-unsaturated ester, and this led to reordering the steps to construct the side-chain intermediate before the epoxidation of 8,9 olefin. It was discovered that the stereochemistry of the triol could be varied by selection of the asymmetric dihydroxylation catalyst and precursor trisubstituted alkene (Scheme 1) used in the dihydroxylation reaction. Use of the (Z)-olefin was expected to lead to the formation of ganodermanontriol and the (24R,25S) diastereomer, while the (E)-olefin was expected to lead to the formation of two other isomeric triols.

It has been reported that use of a methyl-branched phosphonate in the Ando-modified Homer-Wadsworth Emmons (HWE) reaction provides moderate (Z)-stereoselectivity.[16] It was discovered that reaction of the bis(2-tert-butylphenoxy) phosphonate anion occurs at the aldehyde with excellent stereo selectivity to give (Z)-olefin 4Z. The effect of counterions during the deprotonation step was investigated to determine their influence upon (E) or (Z)-selectivity. It was found that NaHMDS appeared to give only the (Z)-olefin in 62% yield, while KHMDS, and LiHMDS both appeared to give an E/Z ratio of 1:9 in 58 and 43% yields, respectively. This result contrasts with the higher Z/E selectivity previously reported with larger counterions during the preparation of disubstituted α,β-unsaturated esters.[17] Selective formation of the (E)-olefin through phosphonate chemistry initially presented difficulties. HWE olefination of 5 using triethyl 2-phosphonopropionate in THF with the addition of LiBr gave 4 with an E/Z ratio of 2:1.[18] It was further observed that preparative scale separation of the (E) and (Z) isomers was difficult to achieve. It was found that the use of (carbethoxyethylidene)triphenylphosphorane gives a much better E/Z ratio of 22:1 in an isolated yield of 79%.[19] It should also be noted that in neither the phosphonate or phosphorane reactions was there any evidence of a reaction at the ketone. Without being bound by theory, selectivity toward the aldehyde is presumed to be driven by the greater electrophilicity and lower steric hindrance relative of the aldehyde relative to the ketone.

Peracid reaction with the unsaturated esters provided 59-62% of 8E/Z, along with starting material and over epoxidized side product. Compounds 8 E/Z were subjected to an improved gentle opening with p-TsOH in toluene for 1 hour. There was no need for purification of diene 9, which was obtained in an isolated yield of 88-90%, following workup. The rate of epoxidation was accelerated using $CHCl_3$ consistent with acid-catalysis.[20]

During reduction to the allylic alcohols, the ketones were protected as 10E/Z with ethylene glycol and p-TsOH during azeotropic distillation (Scheme 3). The esters were reduced using DIBAL under conditions that required careful optimization.[18] At 0° C. with rapid addition of the reductant, the reactions proceeded in 30-40% yield. It was discovered that reducing the reaction temperature to −100° C. coupled with slow addition of DIBAL led to 90-96% yields. Acidic deprotection of the ketals gave the precursors 12 to the isomeric triols. Alcohol 12E is ganoderol A, a natural product that has been reported to have significant hypocholestemic activity in mammalian cells potentially through inhibition of lanosterol 14α demethylase.[7b]

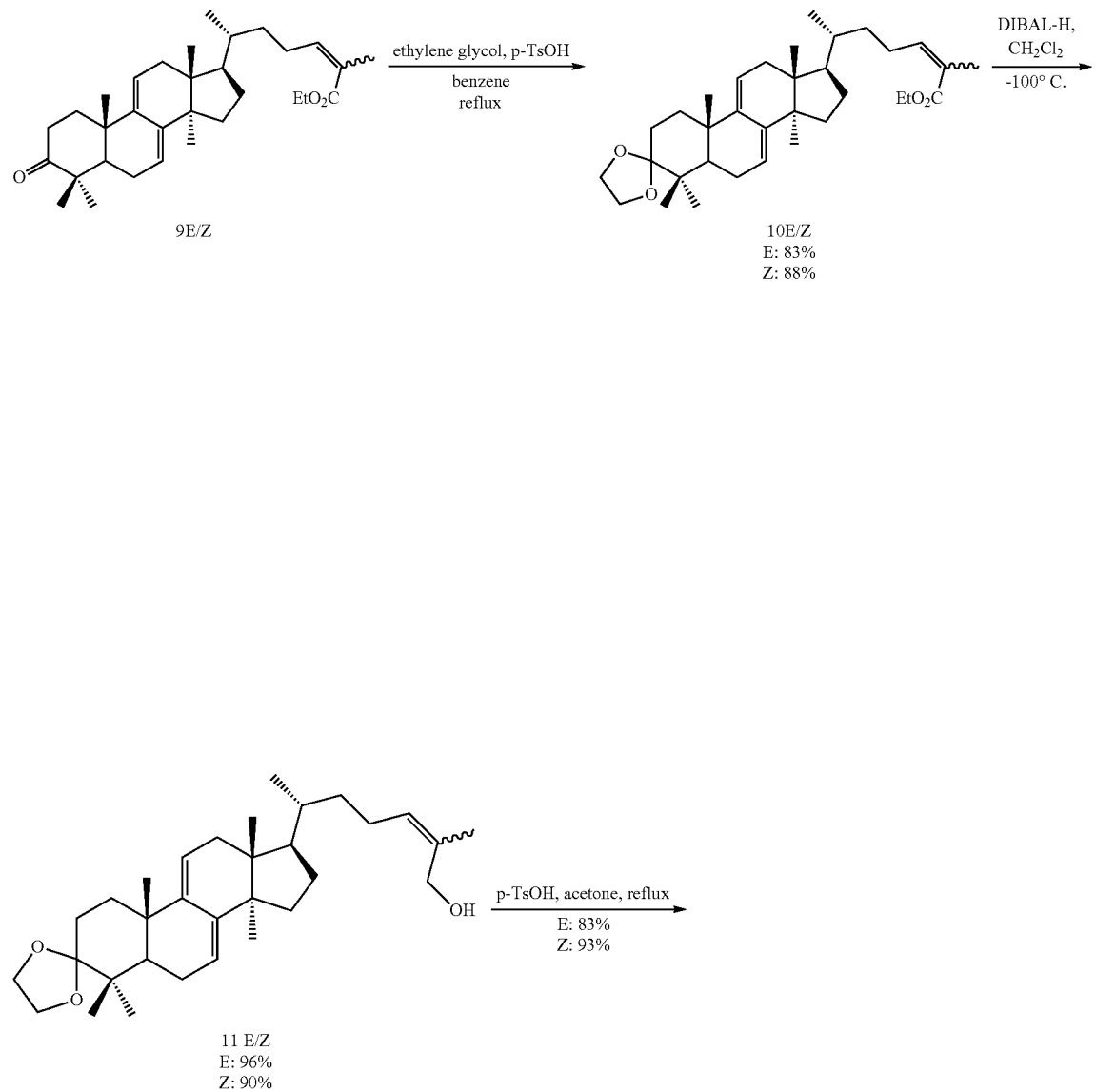

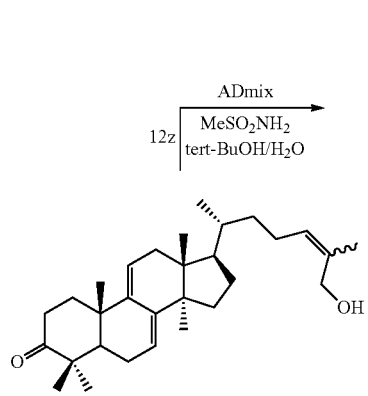
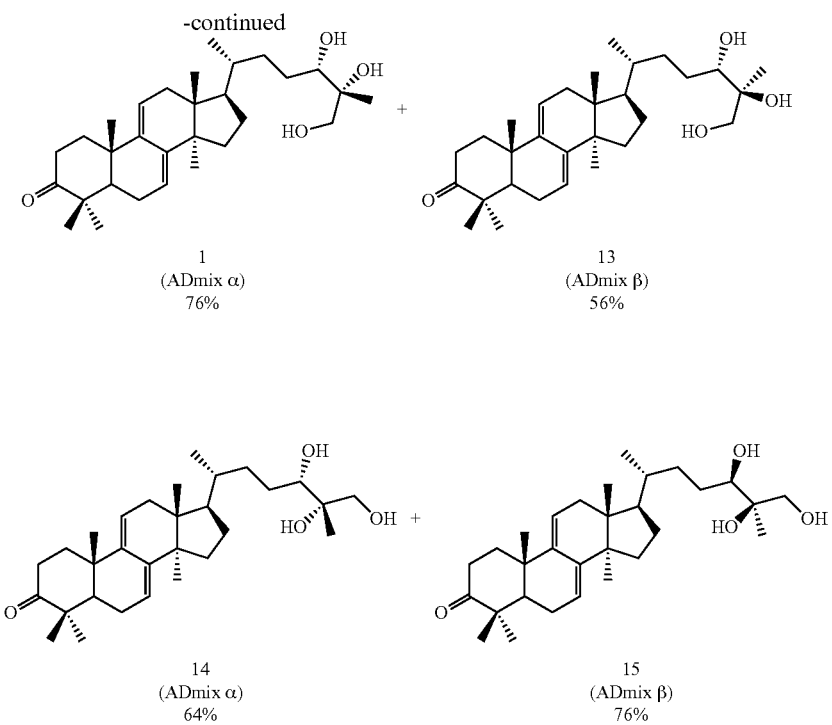

The triols were formed by Sharpless asymmetric dihydroxylation (AD) of 12. Reaction of 12Z and 12E with 2.8 g/mmol of ADmix-β gave 13 and 15, respectively. Similarily, and seemingly consistent with the AD model that requires placement of the smallest group in the southeast quadrant,[21] oxidation of 12Z and 12E with ADmix-α gave 1 and 14, respectively. All spectroscopic data for synthetic 1 was in agreement with literature data.[22] Purification of the AD reactions gave 56-77% yields of the triols. The diastereoselectivities of the dihydroxlation reactions of the (Z)-alkenes were highest; a 17.6:1 ratio was found for the stereomatched reaction with ADmix-β and the de was 10.5:1 for the production of 1. Diastereomeric ratios of the trishydroxy compounds derived from the (E)-isomers were lower at 2.7-5.7:1. These results appear to be consistent with the stereochemical biases for lanosterol and desmosterol ester substrates.[21,23] The (E) isomer was found to be less reactive toward either AD-mix reagent compared to the (Z) isomer. Recovery of residual starting material was readily accomplished. Inductive deactivation of allylic alcohols and ethers versus alkyl-substituted alkenes toward dihydroxylation has been observed when coordination to osmium is blocked, as is the case for ferricyanide-mediated AD-mix reactions.[24] For 13, the rate of side-chain oxidation remains substantially greater than for the diene.

Figure 2:
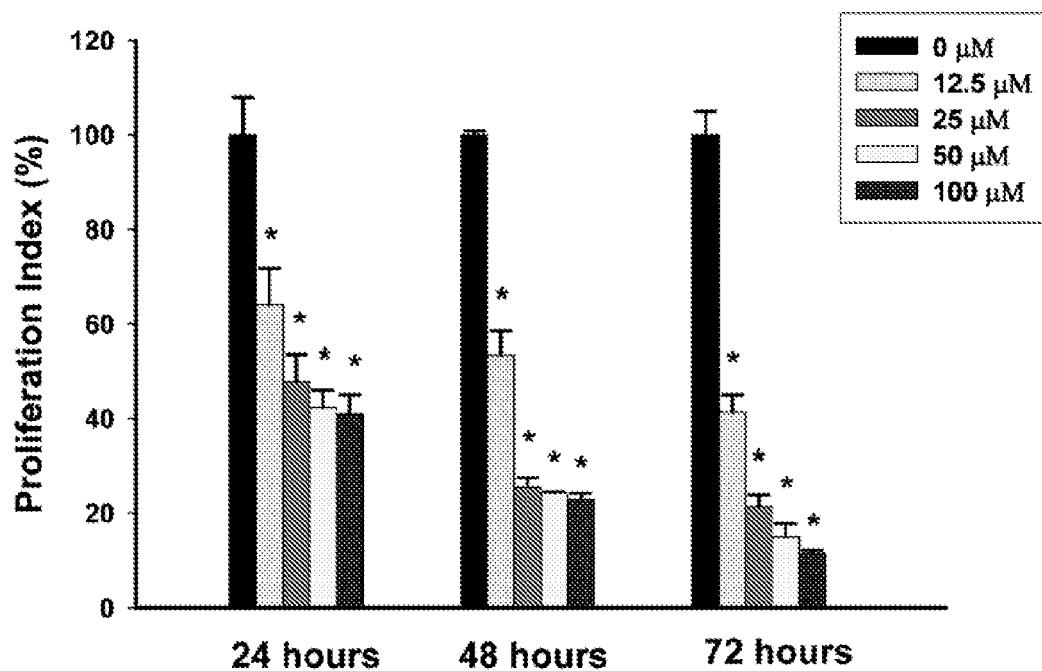
FIG. 2. The effect of *Ganoderma* triterpenes on proliferation of MDA-MB-231 cells. MDA-MB-231 cells are treated with: Panel A ganodermanontriol (compound 1) (0-100 μM), IC$_{50}$ at 72 h=9.7 μM; Panel B compound 13 (0-100 μM), IC$_{50}$ at 72 h=33.8 μM; Panel C compound 14 (0-100 μM), IC$_{50}$ at 72 h=36.7 μM; and Panel D compound 15 (0-100 μM), IC$_{50}$ at 72 h=11.3 μM. Cell proliferation is determined by the tetrazolium salt method. Data are the means±SD of triplicate determinations. Similar results are obtained in at least two additional experiments. *p<0.05
Figure 2:
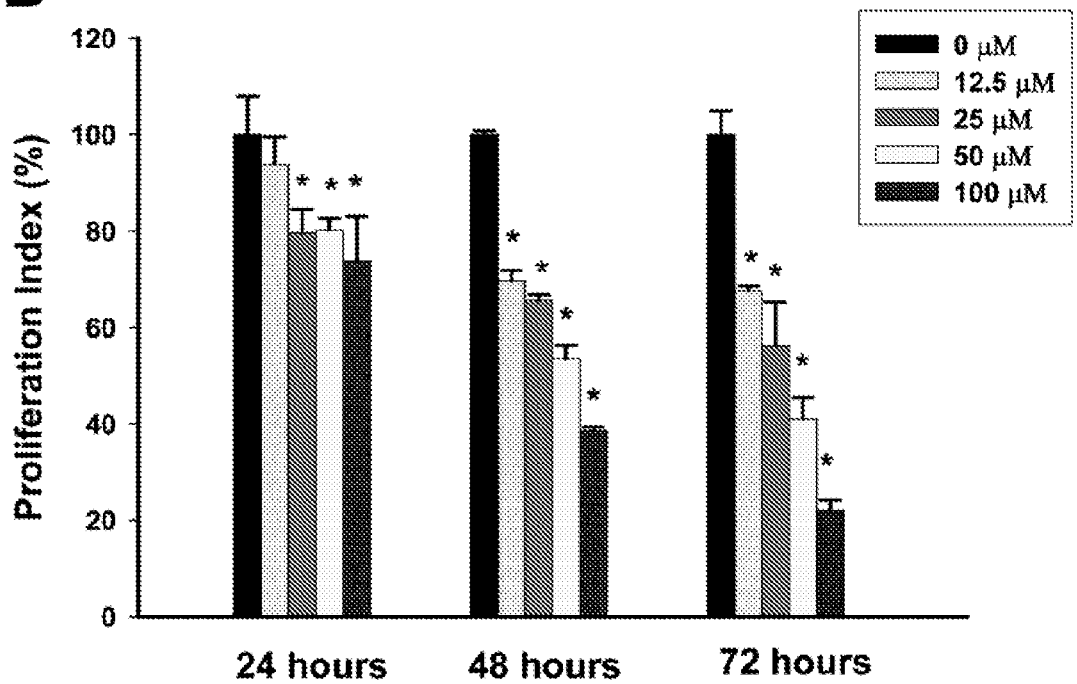
Figure 2:
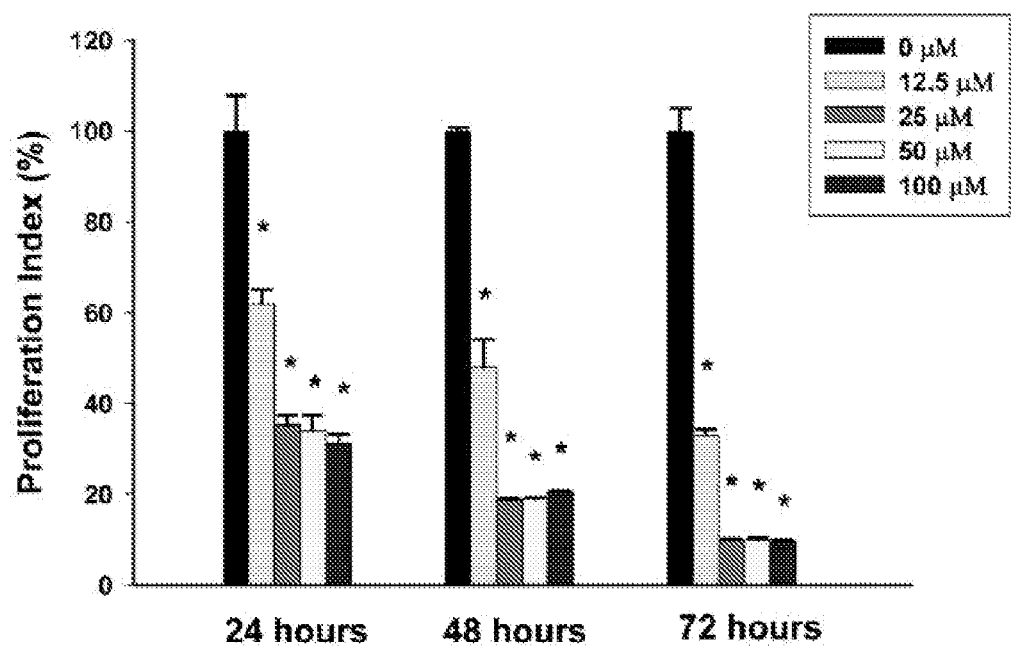
Figure 2:
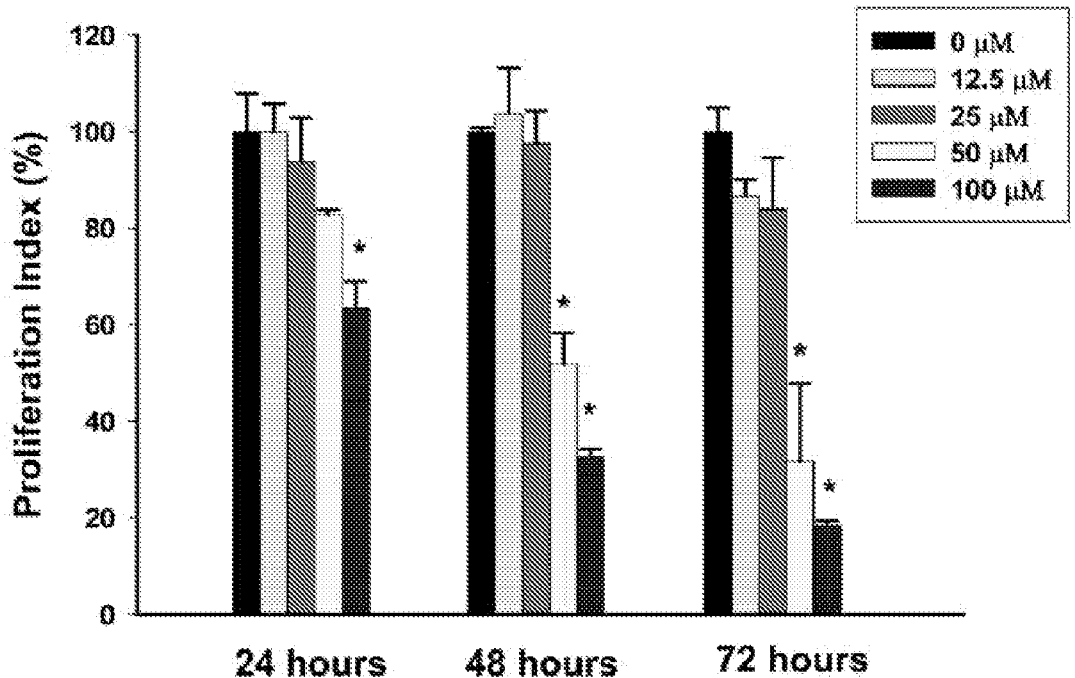

The inhibition of cell proliferation by each of compounds 1, 13, 14, 15, was evaluated on cell lines, MCF-7 (FIG. 1) and MDA-MB-231 (FIG. 2). Ganodermanontriol showed inhibitory activity ($IC_{50}$=5.8 μM at 72 hours) on the proliferation of MCF-7 cancer cells. An $IC_{50}$ value of 9.7 μM was measured for the inhibition of cell proliferation of the MDA-MB-231 cell line. The other isomers also inhibited cell proliferation in cell lines MCF-7 and MDA-MB-231 as shown by their respective $IC_{50}$ values (13: $IC_{50}$=24.1, 33.8 μM, 14: $IC_{50}$=16.3, 36.7 μM, 15: $IC_{50}$=24.1, 11.3 μM).

A process for preparing ganodermanontriol is described herein which provides ganodermanontriol in an overall yield of 15.3% over 9 steps. Processes for preparing the stereoisomeric triols in overall yields in the range of 11.3-14.5% are also described.

Methods

General Information: All reactions were performed under a nitrogen atmosphere with dry solvents in oven-baked or flame-dried glassware, unless otherwise noted. Tetrahydrofuran (THF) was dried by refluxing over sodium and benzophenone. Dichloromethane was distilled from calcium hydride. Triethylamine was distilled from calcium hydride. Anhydrous DMSO was obtained from Acros Organics. Yields are reported for chromatographically homogeneous and spectroscopically pure materials, unless otherwise noted. Unless otherwise indicated, all other reagents were commercially available from Thermo Fisher/ACROS or Sigma-Aldrich and used without further purification. Lanosterol was purchased from Apin Chemicals Ltd. in Abington, Oxon, UK. Ethyl 2-bis(2-tertbutylphenoxy) phosphonopropionate was prepared by the method of Ando.[16c]

Physical Properties and Spectroscopic Measurements: Analytical thin layer chromatography (TLC) was performed on aluminum sheets precoated with a 200 μm thickness of F254 silica gel (Aldrich). The TLC plates were visualized with UV light and/or by staining with p-anisaldehyde solution (2.6 mL p-anisaldehyde+1.1 mL acetic acid+3.6 mL concentrated $H_2SO_4$ diluted to 100 mL with 95% ethanol) or by KMnO4 (1% w/v+6.6% w/v $K_2CO_3$ in 0.082% w/v aqueous NaOH). Silica gel (32-63 microns, Dynamic Adsorbents Inc., Atlanta, Ga.) was slurry packed for flash column chromatography. Melting points were measured using a Thomas Hoover capillary melting point apparatus. Optical rotations were determined on a Perkin-Elmer 241 polarimeter at 20° C. and 589 nm (sodium D-line). IR spectra were recorded using a Nicolet Avatar 330 FT-IR spectrophotometer with either KBr pellets or neat films on a NaCl disc prepared by evaporating a $CH_2Cl_2$ solution of the analyte. $^1H$ and $^{13}C$ nuclear magnetic resonance (NMR) spectra were recorded on a Bruker Avance II spectrometer at 500 and 125 MHz, respectively, and were referenced to residual solvent signals (CHCl$_3$, δ 7.26 ppm and DMSO-d6, δ 2.50 for $^1$H spectra; CHCl$_3$, δ 77.00 ppm for $^{13}$C spectroscopic data). Filtered (DEPT-135, DEPT-90) and z-gradient two-dimensional (2D) NMR experiments (gsHSQC, gsHMBC, and gsCOSY90) were conducted using standard pulse sequences. Atmospheric pressure chemical ionization (APCI) high-resolution mass spectrometry (HRMS) data were recorded on an Agilent 1200 LC-6520 QTOF MS using the manufacturer's internal reference solution.

(4R)-4-((10S,13R,14R,17R)-4,4,10,13,14-Pentamethyl-3-oxo-2,3,4,5,6,7,10,11,12,13,14,15,16,17-tetradecahydro-1H-cyclopenta[a]phenanthren-17-yl)pentanal (Lanosterone, 7). A solution of oxalyl chloride (4.60 mL, 53.4 mmol, 2.2 equiv) in CH$_2$Cl$_2$ (61 mL) was placed in a 100-mL three-neck round-bottom flask equipped with a thermometer and a magnetic stir bar. Dimethylsulfoxide (8.30 mL, 116 mmol, 4.8 equiv) was dissolved in CH$_2$Cl$_2$ (12.1 mL) and added slowly by a dropping funnel to the stirred oxalyl chloride solution at a temperature between −50 and −60° C. in a dry ice/acetone bath. This temperature was maintained for 4 min. Next, a solution of lanosterol (10.352 g, 24.258 mmol, 1.0 equiv) in DMSO (7 mL) and CH$_2$Cl$_2$ (55 mL) was added in one portion by dropping funnel to the stirred reaction mixture. The bath was switched to dry ice/ethylene glycol and the temperature was increased to ca. −20° C. and allowed to react at this temperature for 2 min. Triethylamine (16.9 mL, 121 mmol, 5.0 equiv) was added and stirred for 5 min before removing the cooling bath and allowing the mixture to warm to room temperature. Water (50 mL) was added, the phases separated, and the aqueous layer was extracted with CH$_2$Cl$_2$ (50 mL). The combined organic layers were washed twice with a 1 N HCl (50 mL), water (50 mL), a 1% aqueous sodium bicarbonate (50 mL), and finally saturated NaCl solution (50 mL). The CH$_2$Cl$_2$ solution was then dried with anhydrous MgSO$_4$, filtered through a pad of Celite and concentrated with rotary evaporator to afford 7 as a brownish-yellow solid (9.85 g). This mixture, which contains both lanosterone and dihydrolanosterone, was carried to the ozonolysis step without further purification. IR (KBr) ν$_{max}$ 2951, 1708, 1465, 1377, 1271, 1114 cm$^{-1}$. $^{13}$C{$^1$H} δ (CDCl$_3$, mixture of ketones) 217.9, 135.3, 133.1, 130.9, 125.2, 51.2, 50.5, 50.4, 49.9, 47.4, 44.5, 44.4, 39.5, 36.9, 36.5, 36.4, 36.3, 36.2, 36.1, 34.6, 30.9, 30.9, 28.2, 28.0, 26.3, 26.2, 25.7, 24.9, 24.3, 24.1, 22.8, 22.5, 21.9, 21.1, 19.4, 18.7, 18.7, 18.6, 15.8.

(4R)-4-((10S,13R,14R,17R)-4,4,10,13,14-Pentamethyl-3-oxo-2,3,4,5,6,7,10,11,12,13,14,15,16,17-tetradecahydro-1H-cyclopenta[a]phenanthren-17-yl)pentanal (5). A solution of lanosterone (4.27 g, 9.11 mmol) in CH$_2$Cl$_2$ (128 mL) was placed in a three-neck round bottom flask equipped with a magnetic stir bar, thermometer, a CaCl$_2$ drying tube and a gas inlet tube. The mixture was stirred and cooled to −50° C., at which point ozone was passed through the mixture for 17 min. The reaction mixture was then purged with argon for 20 min and then concentrated in vacuo to ca. 5 mL. After diluting the crude material with CH$_2$Cl$_2$ (50 mL), the organic phase was then washed twice with water (50 mL) and dried with anhydrous MgSO$_4$. The crude product was concentrated with a rotary evaporator and purified by silica gel chromatography (step gradient of 5:1 then 3:1 hexane/EtOAc) to afford 5 as a white solid (1.578 g, 3.958 mmol, 78% based on an initial purity of 56% for the commercial lanosterol). mp 110-115° C. IR (KBr) ν$_{max}$ 2722, 1725, 1709 cm$^{-1}$. $^1$H NMR (CDCl$_3$) δ 9.77 (t, J=1.9 Hz, 1H), 2.57 (ddd, J=7.1, 11.2, 15.7 Hz, 1H), 2.5-2.3 (m, 3H), 2.10-1.18 (m, 19H), 1.11 (s, 3H), 1.09 (s, 3H), 1.06 (s, 3H), 0.90 (d, J=6.3 Hz, 3H), 0.89 (s, 3H), 0.71 (s, 3H). $^{13}$C{$^1$H} δ (CDCl$_3$) δ 217.8, 203.2, 135.2, 133.2, 51.2, 50.3, 49.9, 47.4, 44.5, 41.1, 36.9, 36.1, 36.0, 34.6, 30.90, 30.87, 28.2, 28.11, 26.33, 26.2, 24.3, 21.3, 21.1, 19.4, 18.7, 18.4, 15.9. HRMS calcd for C$_{27}$H$_{43}$O$_2$ (M+H)$^+$ 399.3258. found 399.3258.

Ethyl (6R,Z)-2-methyl-6-((10S,13R,14R,17R)-4,4,10,13,14-pentamethyl-3-oxo-2,3,4,5,6,7,10,11,12,13,14,15,16,17-tetradecahydro-1H-cyclopenta[a]phenanthren-17-yl)hept-2-enoate (4Z). To a stirred solution of phosphonate ester (0.463 g, 1.04 mmol, 1.0 equiv) in THF (21 mL) cooled in an ice-water bath was added NaHMDS (1.04 mL, 1.0 M in solvent, 1.04 mmol, 1.0 equiv) at 0° C. and the deprotonation was allowed to proceed for 1 h. A solution of aldehyde (0.413 g, 1.04 mmol, 1.0 equiv) in THF (21 mL) was added in one portion to the reaction mixture at −78° C. The solution was stirred for 20 min and was then allowed to warm to room temperature and stirring was continued for 12 h. The resulting solution was then diluted with CH$_2$Cl$_2$ (50 mL) and washed twice with saturated ammonium chloride solution (50 mL). The organic phase was dried with anhydrous MgSO$_4$, vacuum filtered, and the filtrate evaporated under reduced pressure. The sample was purified by silica gel chromatography (step gradient of 20:1:1 to 8:1:1 hexane:EtOAc:CH$_2$Cl$_2$) to afford 4 as a pure white crystalline solid (0.311 g, 0.645 mmol) in 62% yield. mp 86-89° C. IR (KBr) ν$_{max}$ 2952, 2872, 2842, 1710 (C=O, unsaturated ester and ketone), 1644 cm$^{-1}$. $^1$H NMR (CDCl$_3$) δ 5.90 (qt, J=1.5, 7.5 Hz, 1H), 4.20 (q, J=7.1 Hz, 2H), 2.57 (ddd, J=7.0, 11.1, 15.5 Hz, 1H), 2.50 (m, 1H), 2.43-2.34 (m, 2H), 2.1-1.9 (m, 6H), 1.79-1.58 (m, 8H), 1.51-1.33 (m, 4H), 1.89 (d, J=1.1 Hz, 3H), 1.31 (t, J=7.1 Hz, 3H), 1.20 (m, 1H), 1.12 (s, 3H), 1.09 (s, 3H), 1.06 (s, 3H), 0.93 (d, J=6.3 Hz, 3H), 0.89 (s, 3H), 0.71 (s, 3H). $^{13}$C{$^1$H} (CDCl$_3$) δ 217.9, 168.3, 143.4, 135.3, 133.2, 126.8, 60.0, 51.2, 50.4, 49.9, 47.4, 44.5, 36.9, 36.4, 36.1, 35.9, 34.6, 30.91, 30.90, 28.2, 26.6, 26.3, 26.2, 24.3, 21.3, 21.1, 20.7, 19.4, 18.7, 18.5, 15.8, 14.3. HRMS calcd for C$_{32}$H$_{51}$O$_3$ (M+H)$^+$ 483.3833. found 483.3826.

Ethyl (6R,E)-2-methyl-6-((10S,13R,14R,17R)-4,4,10,13,14-pentamethyl-3-oxo-2,3,4,5,6,7,10,11,12,13,14,15,16,17-tetradecahydro-1H-cyclopenta[a]phenanthren-17-yl)hept-2-enoate (4E). A mixture of aldehyde (0.925 g, 2.32 mmol, 1.0 equiv) and (carbethoxyethylidene)triphenylphosphorane (0.925 g, 2.32 mmol, 1.1 equiv) was stirred overnight in CH$_2$Cl$_2$ (23 mL) at 25° C. and then concentrated in vacuo. The mixture was then purified by silica gel chromatography (5:1:1 n-hexane/EtOAc/CH$_2$Cl$_2$) to afford the ester as a clear oil (0.131 g, 71%). IR (NaCl) ν$_{max}$ 2953, 2869, 1706 (C=O, unsaturated ester and ketone), 1644 cm$^{-1}$. $^1$H NMR (CDCl$^3$) δ 6.69 (dt, J=1.3, 7.5 Hz, 1H), 4.13 (q, J=7.1 Hz, 2H), 2.52 (ddd, J=7.1, 8.6, 15.7 Hz, 1H), 2.34 (ddd, J=3.5, 6.8, 15.7 Hz, 1H), 2.10 (m, 1H), 2.20-1.80 (m, 9H), 1.76 (d, J=1.0 Hz, 3H), 1.8-1.3 (m, 11H), 1.22 (t, J=7.1 Hz, 3H), 1.05 (s, 3H), 1.02 (s, 3H), 1.00 (s, 3H), 0.87 (d, J=6.3 Hz, 3H), 0.82 (s, 3H), 0.65 (s, 3H). 13C (CDCl$^3$) δ 216.9, 167.3, 141.8, 134.3, 132.2, 126.4, 59.4, 50.2, 49.3, 48.9, 46.4, 43.5, 35.9, 35.3, 35.0, 33.9, 33.6, 29.92, 29.87, 27.1, 25.3, 25.2, 24.6, 23.3, 20.3, 20.1, 18.4, 17.7, 17.5, 14.8, 13.3, 11.3. HRMS calcd for C$_{32}$H$_{51}$O$_3$ (M+H)$^+$ 483.3833. found 483.3833.

General Epoxidation Procedure. A mixture of ester 4E (0.444 g, 0.920 mmol, 1.0 equiv) and mCPBA (0.212 g, 0.920 mmol, 75%, 1.0 equiv) in CHCl$_3$ (16.0 mL) was stirred for 12 h at 25° C. The reaction was then quenched with solid Ca(OH)$_2$ (0.273 g, 3.68 mmol, 4.0 equiv) and Na$_2$SO$_4$ (0.523 g, 3.68 mmol, 4.0 equiv). This mixture was then stirred for 75 min. The solid was then filtered off, and the filtrate was concentrated with a rotary evaporator. The oily residue was then purified by silica gel chromatography (5:1:1 n-hexane:

EtOAc:CH$_2$Cl$_2$) to afford 8E as a clear oil (0.268 g, 59% yield). Ester 8Z was prepared by an analogous procedure to afford 8Z as a white crystal in 62% yield.

Ethyl (6R,E)-2-methyl-6-((10S,13R,14R,17R)-4,4,10,13,14-pentamethyl-3-oxotetradecahydro-1H-8,9-epoxycyclopenta[a]phenanthren-17-yl)hept-2-enoate (8E): IR (NaCl) $\nu_{max}$ 2958, 2880, 1708, 1646, 1459 cm$^{-1}$. $^1$H NMR (CDCl$_3$) δ 6.73 (qt, J=1.2, 7.5 Hz, 1H), 4.18 (q, J=7.1 Hz, 1H) 2.55 (m, 1H), 2.42 (m, 1H) 2.11-1.85 (m, 9H), 1.82 (br s, 3H), 1.74 (dd, J=6.4, 15.2 Hz, 1H), 1.60 (s, 3H), 1.64-1.26 (m, 8H) 1.29 (t, J=7.1 Hz, 3H), 1.25 (s, 3H), 1.15 (m, 1H), 1.03 (s, 3H), 1.01 (s, 3H), 0.92 (d, J=6.2 Hz, 3H), 0.89 (s, 3H), 0.79 (s, 3H). $^{13}$C{$^1$H} (CDCl$_3$) δ 216.7, 168.3, 142.6, 127.5, 70.5, 68.5, 60.4, 48.9, 48.2, 46.9, 43.7, 43.3, 37.7, 36.0, 34.8, 34.0, 33.2, 32.1, 28.4, 26.8, 26.6, 25.5, 23.9, 21.5, 20.9, 19.9, 18.7, 17.7, 16.8, 16.3, 14.3, 12.3. HRMS calcd for C$_{32}$H$_{51}$O$_4$ (M+H)$^+$ 499.3782. found 499.3775.

Ethyl (6R,Z)-2-methyl-6-((10S,13R,14R,17R)-4,4,10,13,14-pentamethyl-3-oxotetradecahydro-1H-8,9-epoxycyclopenta[a]phenanthren-17-yl)hept-2-enoate (8Z): mp 68-70° C. IR (KBr) $\nu_{max}$ 2952, 2883, 1707, 1652, 1456 cm$^{-1}$. $^1$H NMR (CDCl$_3$) δ 5.88 (dt, J=1.3, 7.7 Hz, 1H), 4.19 (q, J=7.2 Hz, 2H), 2.56 (m, 1H), 2.51-2.32 (m, 3H), 2.08 (dd, J=3.3, 12.5 Hz, 1H), 2.06-1.81 (m, 6H), 1.88 (d, J=0.9 Hz, 3H), 1.74 (dd, J=6.4, 15.2 Hz, 1H), 1.63-1.32 (m, 9H), 1.29 (t, J=7.1 Hz, 3H), 1.24 (s, 3H), 1.15-1.06 (m, 2H), 1.03 (s, 3H), 1.01 (s, 3H), 0.90 (d, J=6.3 Hz, 3H), 0.89 (s, 3H), 0.78 (s, 3H). $^{13}$C{$^1$H} (CDCl$_3$) δ 216.7, 168.1, 143.3, 126.9, 70.5, 68.6, 60.0, 48.9, 48.2, 47.0, 43.7, 43.3, 37.7, 36.2, 35.8, 34.1, 33.2, 32.2, 28.4, 26.8, 26.62, 26.60, 23.9, 21.5, 20.9, 20.7, 19.9, 18.8, 17.7, 16.9, 16.3, 14.3. HRMS calcd for C$_{32}$H$_{51}$O$_4$ (M+H)$^+$ 499.3782. found 499.3775.

General Epoxide Opening. A mixture of epoxide (0.373 g, 0.748 mmol, 1.0 equiv) and p-toluenesulfonic acid (0.00142 g, 0.0748 mmol, 0.1 equiv) in toluene was stirred for 1 h at 60° C. The reaction was then quenched with triethylamine (10.4 μL, 0.0748 mmol, 0.1 equiv). The salt was then filtered off on a pad of silica gel and Celite using toluene to afford 9E as a pure white crystalline solid (0.311 g, 88% yield). Diene 9Z was prepared by an analogous procedure in 91% yield.

Ethyl (6R,E)-2-methyl-6-((10S,13R,14R,17R)-4,4,10,13,14-pentamethyl-3-oxo 2,3,4,5,6,10,12,13,14,15,16,17-dodecahydro-1H-cyclopenta[a]phenanthren-17-yl)hept-2-enoate (9E): mp 53-55° C. IR (KBr) $\nu_{max}$ 3039, 2963, 2932, 2883, 1710 (C═O, unsaturated ester and ketone), 1652 cm$^{-1}$. $^1$H NMR (CDCl$_3$) δ 6.75 (dt, J=1.4, 7.5 Hz, 1H), 5.51 (d, J=6.8 Hz, 1H), 5.39 (d, J=6.3 Hz, 1H), 4.18 (q, J=7.1 Hz, 2H), 2.78 (dt, J=5.8, 14.6 Hz, 1H), 2.34 (ddd, J=3.2, 4.4, 14.8 Hz, 1H), 2.3-1.9 (m, 8H), 1.84 (d, J=0.7 Hz, 3H), 1.76 (dt, J=4.5, 13.9 Hz, 1H), 1.65-1.31 (m, 9H), 1.29 (t, J=7.1 Hz, 3H), 1.20 (s, 3H), 1.13 (s, 3H), 1.09 (s, 3H), 0.93 (d, J=6.5 Hz, 3H), 0.87 (s, 3H), 0.59 (s, 3H). $^{13}$C{$^1$H} (CDCl$_3$) δ 216.8, 168.4, 144.5, 142.8, 142.7, 127.5, 119.9, 117.2, 60.4, 50.8, 50.7, 50.3, 47.5, 43.8, 37.8, 37.2, 36.6, 36.2, 34.89, 34.85, 31.5, 27.9, 25.7, 25.4, 25.3, 23.7, 22.5, 22.1, 18.3, 15.7, 14.3, 12.3. HRMS calcd for C$_{32}$H$_{49}$O$_3$ (M+H)$^+$ 481.3676. found 481.3655.

Ethyl (6R,Z)-2-methyl-6-((10S,13R,14R,17R)-4,4,10,13,14-pentamethyl-3-oxo-2,3,4,5,6,10,12,13,14,15,16,17-dodecahydro-1H-cyclopenta[a]phenanthren-17-yl)hept-2-enoate (9Z): mp 128-129° C. IR (KBr) $\nu_{max}$ 3035, 2960, 2931, 2878, 1712 (C═O, unsaturated ester and ketone), 1645 cm$^{-1}$. $^1$H NMR (CDCl$_3$) δ 5.89 (dt, J=1.5, 7.5 Hz, 1H), 5.50 (d, J=6.5 Hz, 1H), 5.38 (d, J=6.0 Hz, 1H), 4.20 (q, J=7.1 Hz, 2H), 2.77 (dt, J=5.7, 14.5 Hz, 1H), 2.55-1.93 (m, 9H), 1.89 (d, J=1.0 Hz, 3H), 1.76 (dt, J=4.5, 13.8 Hz, 1H), 1.66-1.31 (m, 8H), 1.30 (t, J=7.1 Hz, 3H), 1.20 (s, 3H), 1.13 (s, 3H), 1.09 (s, 3H), 0.92 (d, J=6.5 Hz, 3H), 0.87 (s, 3H), 0.59 (s, 3H). $^{13}$C{$^1$H} (CDCl$_3$) δ 216.8, 168.2, 144.5, 143.4, 142.9, 126.9, 119.9, 117.3, 60.0, 50.9, 50.7, 50.3, 47.5, 42.8, 37.8, 37.2, 36.6, 36.2, 35.8, 34.8, 31.5, 27.9, 26.7, 25.43, 25.40, 23.7, 22.5, 22.1, 20.7, 18.4, 15.7, 14.3. HRMS calcd for C$_{32}$H$_{49}$O$_3$ (M+H)$^+$ 481.3676. found 481.3678.

General Ketalization. Ketone 9E (0.257 g, 0.535 mmol, 1.0 equiv) was dissolved in benzene (27 mL). After the ketone was completely dissolved, p-toluenesulfonic acid (0.0102 g, 0.0535 mmol, 0.1 equiv) and ethylene glycol (0.298 mL, 5.35 mmol, 10 equiv) were added and the solution was heated to reflux for 20 h using a modified Dean-Stark apparatus. The mixture was then allowed to cool to room temperature, and was then concentrated using a rotary evaporator. The residue was then diluted with CH$_2$Cl$_2$ (30 mL) and washed with saturated sodium bicarbonate solution (3×30 mL). The organic layer was washed with a saturated brine (30 mL), dried with MgSO$_4$, and vacuum filtered through a pad of Celite. The filtrate was concentrated with a rotary evaporator to give 10E as a pure white crystalline product (0.246 g, 88% yield). 10Z was prepared by an analogous procedure in 83% yield. (6R,E)-Ethyl-2-methyl-6-((10S,13R,14R,17R)-4,4,10,13,14-pentamethyl-1,2,4,5,6,10,12,13,14,15,16,17-dodecahydrospiro[cyclopenta[a]phenanthrene-3,2'-[1,3]dioxolan]-17-yl)hept-2-enoate (10E): mp 75-79° C. IR (KBr) $\nu_{max}$ 3047, 2963, 2924, 2898, 2888, 1705, 1652, 1197, 1141, 1101, 1098, 1050, 1028, 964, 952 cm$^{-1}$. $^1$H NMR (CDCl$_3$) δ 6.75 (dt, J=1.3, 7.5 Hz, 1H), 5.45 (m, 1H), 5.31 (d, J=6.3 Hz, 1H), 4.18 (q, J=7.1 Hz, 2H), 3.96 (m, 3H), 3.88 (m, 1H), 2.27-2.17 (m, 2H), 2.11-1.84 (m, 8H), 1.81 (d, J=1.1 Hz, 3H), 1.75-1.31 (m, 7H), 1.29 (t, J=7.1 Hz, 3H), 1.22-1.1 (m, 2H), 1.04 (s, 3H), 1.02 (s, 3H), 0.92 (d, J=6.5 Hz, 3H), 0.88 (s, 3H), 0.86 (s, 3H), 0.60 (s, 3H). $^{13}$C{$^1$H} (CDCl$_3$) δ 168.3, 145.9, 142.8, 142.5, 127.4, 120.2, 116.0, 113.1, 64.9, 64.7, 60.4, 50.8, 50.3, 47.4, 43.8, 41.8, 37.8, 37.0, 36.2, 34.9, 34.0, 31.5, 27.9, 27.2, 25.7, 25.6, 23.1, 22.9, 22.7, 20.4, 18.3, 15.6, 14.3, 12.3. HRMS calcd for C$_{34}$H$_{53}$O$_4$ (M+H)$^+$ 525.3938. found 525.3922.

(6R,Z)-Ethyl-2-methyl-6-((10S,13R,14R,17R)-4,4,10,13,14-pentamethyl-1,2,4,5,6,10,12,13,14,15,16,17-dodecahydrospiro[cyclopenta[a]phenanthrene-3,2'-[1,3]dioxolan]-17-yl)hept-2-enoate (10Z): mp 80-84° C. IR (KBr) $\nu_{max}$ 3039, 2964, 2923, 2878, 2837, 1707, 1645, 1261, 1196, 1155, 1099, 1053, 1028 cm$^{-1}$. $^1$H NMR (CDCl$_3$) δ 5.91 (dt, J=1.3, 7.5 Hz, 1H), 5.45 (br s, 1H), 5.30 (d, J=6.3 Hz, 1H), 4.20 (q, J=7.1 Hz, 2H), 3.96 (m, 3H), 3.89 (m, 1H), 2.50 (m, 1H), 2.20 (m, 1H), 2.2 (d, J=17.5 Hz, 1H), 2.17-1.35 (m, 17H), 1.32 (t, J=7.2 Hz, 3H), 1.19-1.05 (m, 2H), 1.04 (s, 3H), 1.02 (s, 3H), 0.91 (d, J=6.5 Hz, 3H), 0.88 (s, 3H), 0.86 (s, 3H), 0.57 (s, 3H). 13C (CDCl$_3$) δ 168.3, 145.9, 143.4, 142.6, 126.8, 120.1, 116.1, 113.2, 64.9, 64.7, 60.0, 50.9, 50.4, 47.4, 43.8, 41.9, 37.8, 37.0, 36.2, 35.9, 34.0, 31.5, 27.9, 27.2, 26.7, 25.7, 23.2, 22.9, 22.7, 20.7, 20.4, 18.3, 15.7, 14.3. HRMS calcd for C$_{34}$H$_{53}$O$_4$ (M+H)$^+$ 525.3938. found 525.3922.

General Reduction of Ester. In a round-bottom flask containing a magnetic stir bar, ester 10E (0.223 g, 0.425 mmol, 1.0 equiv) was dissolved in CH$_2$Cl$_2$ (1.7 mL) and cooled to −100° C. Diisobutylaluminum hydride (1.31 mL, 0.97 M solution in hexanes, 1.28 mmol, 3.0 equiv) dropwise with the aid of a syringe pump over 12 min. After 40 min had elapsed, saturated NH$_4$Cl solution (4 mL) was added and the quenched reaction mixture was warmed to room temperature and stirred overnight. A white precipitate ensued that was removed by filtration with a Celite-packed Büchner funnel. The contents of the funnel were washed with CH$_2$Cl$_2$ (15 mL). and the combined organic layers were then separated from the aqueous solution, and then washed with saturated brine (30 mL). The CH$_2$Cl$_2$ solution was dried over MgSO$_4$, vacuum filtered, and concentrated with a rotary evaporator to give 11E as a pure white crystalline product (0.197 g, 96% yield). Alcohol 11Z was made by an analogous procedure in 90% yield.

(6R,E)-2-Methyl-6-((10S,13R,14R,17R)-4,4,10,13,14-pentamethyl-1,2,4,5,6,10,12,13,14,15,16,17-dodecahydrospiro[cyclopenta[a]phenanthrene-3,2'-[1,3]dioxolan]-17-yl)hept-2-en-1-ol (11E): mp 165-168° C. IR (KBr) $v_{max}$ 3495 (br) 3047, 2957, 2923, 2880, 2837, 1137, 1107, 1054, 1028, 1013, 964 cm$^{-1}$. $^1$H NMR (CDCl$_3$) δ 5.46 (m, 1H), 5.40 (m, 1H), 5.32 (m, 1H), 4.00 (d, J=6 Hz, 2H), 3.96 (m, 3H), 3.89 (m, 1H), 2.2 (d, J=17.5 Hz, 1H), 2.2-2.01 (m, 4H), 2.0-1.84 (m, 4H), 1.72 (dd, J=4, 8.5 Hz, 1H), 1.67 (m, 3H), 1.63-1.23 (m, 10H), 1.09 (m, 1H), 1.04 (s, 3H), 1.02 (s, 3H), 0.91 (d, J=6.5 Hz, 3H), 0.88 (s, 3H), 0.86 (s, 3H), 0.57 (s, 3H). $^{13}$C{$^1$H} (CDCl$_3$) δ 145.9, 142.6, 134.3, 127.0, 120.1, 116.1, 113.2, 69.1, 64.9, 64.7, 50.9, 50.4, 47.4, 43.8, 41.9, 37.8, 37.9, 36.1, 35.8, 34.0, 31.5, 27.9, 27.2, 25.7, 24.5, 23.2, 22.9, 22.7, 20.4, 18.4, 15.7, 13.7. HRMS calcd for C$_{32}$H$_{51}$O$_3$ (M+H)$^+$ 483.3833. found 483.3826.

(6R,Z)-2-Methyl-6-((10S,13R,14R,17R)-4,4,10,13,14-pentamethyl-1,2,4,5,6,10,12,13,14,15,16,17-dodecahydrospiro[cyclopenta[a]phenanthrene-3,2'-[1,3]dioxolan]-17-yl)hept-2-en-1-ol (11Z): mp 148-150° C. IR (KBr) $v_{max}$ 3459 (br), 3044, 2963, 2923, 2981, 2838, 1163, 1136, 1107, 1052, 1029, 1013, 964 cm$^{-1}$. $^1$H NMR (CDCl$_3$) δ 5.39 (m, 1H), 5.24 (m, 2H), 4.07 (m, 2H), 3.89 (m, 3H), 3.82 (m, 1H), 2.15-1.78 (m, 9H), 1.73 (br s, 3H), 1.68-1.18 (m, 11H), 0.97 (s, 3H), 0.95 (s, 3H), 0.83 (d, J=6.5 Hz, 3H), 0.81 (s, 3H), 0.79 (s, 3H), 0.50 (s, 3H). $^{13}$C{$^1$H} (CDCl$_3$) δ 145.9, 142.6, 133.9, 129.2, 120.2, 116.1, 113.2, 64.9, 64.7, 61.7, 50.9, 50.4, 47.4, 43.8, 41.9, 37.8, 37.0, 36.6, 36.0, 34.0, 31.5, 27.9, 27.2, 25.7, 24.5, 23.2, 22.9, 22.7, 21.3, 20.4, 18.4, 15.7. HRMS calcd for C$_{32}$H$_{49}$O$_2$ (M+H–H$_2$O)$^+$ 465.3727. found 465.3689.

Deprotection of Ketal. Alcohol 11E (0.165 g, 0.342 mmol, 1.0 equiv) was dissolved in acetone (10 mL). To this solution, p-toluenesulfonic acid (0.0065 g, 0.034 mmol, 0.01 equiv) was added and stirred 24 h at reflux. Acetone was then removed via a rotary evaporator. The residual solid was then diluted with CH$_2$Cl$_2$ (10 mL) and washed with saturated sodium bicarbonate solution (2×10 mL) followed by saturated brine (10 mL). The organic layer was then dried over MgSO$_4$, vacuum filtered through a pad of Celite, and the resulting filtrate was then concentrated using a rotary evaporator to give 12E as a whitish-yellow crystalline solid (0.124 g, 83% yield). 12Z was made by an analogous procedure in 93% yield.

(10S,13R,14R,17R)-17-((R,E)-7-Hydroxy-6-methylhept-5-en-2-yl)-4,4,10,13,14-pentamethyl-4,5,6,10,12,13,14,15,16,17-decahydro-1H-cyclopenta[a]phenanthren-3(2H)-one (12E): mp 75-80° C. IR (KBr) $v_{max}$ 3445 (br), 3042, 2963, 2931, 2878, 1708, 1634 cm$^{-1}$. $^1$H NMR (CDCl$_3$) δ 5.50 (d, J=6.6 Hz, 1H), 5.39 (m, 2H), 4.00 (s, 2H), 2.77 (dt, J=5.8, 14.7 Hz, 1H), 2.34 (m, 1H), 2.30-1.90 (m, 9H), 1.78 (dt, J=4.3, 13.7 Hz, 1H), 1.67 (s, 3H), 1.65-1.23 (m, 8H), 1.20 (s, 3H), 1.12 (s, 3H), 1.08 (s, 3H), 0.92 (d, J=6.4 Hz, 3H), 0.87 (s, 3H), 0.59 (s, 3H). $^{13}$C{$^1$H} (CDCl$_3$) δ 216.8, 144.5, 142.9, 134.4, 126.9, 119.9, 117.3, 69.1, 50.9, 50.7, 50.3, 47.5, 43.7, 37.8, 37.2, 36.6, 36.0, 35.9, 34.8, 31.4, 27.9, 25.4, 25.3, 24.5, 23.6, 22.4, 22.0, 18.4, 15.7, 13.6. HRMS calcd for C$_{30}$H$_{45}$O (M–H$_2$O)$^+$ 421.3485. found 421.3451.

Literature Data: Ganoderol A: $^1$H NMR (300 MHz, CDCl$_3$) δ 5.60 (1H), 5.40 (1H), 5.39 (1H), 4.10 (2H), 2.80 (1H), 1.70 (3H), 1.22 (3H), 1.13 (3H), 1.09 (3H), 0.92 (3H), 0.88 (3H), 0.59 (3H). $^{13}$C{$^1$H} (CDCl$_3$, referenced to 77.7) δ 216.80, 144.55, 142.90, 134.40, 126.90, 119.90, 69.10, 50.95, 50.75, 50.35, 47.50, 43.90, 37.88, 37.25, 36.10, 35.95, 34.90, 31.50, 27.91, 25.48, 25.39, 24.59, 23.70, 22.52, 22.10, 18.45, 17.30 (data erroneously ascribed to vinyl C-11 in reference), 15.78, 13.70.[7b] (10S,13R,14R,17R)-17-((R,Z)-7-Hydroxy-6-methylhept-5-en-2-yl)-4,4,10,13,14-pentamethyl-4,5,6,10,12,13,14,15,16,17-decahydro-1H-cyclopenta[a]phenanthren-3(2H)-one (12Z): mp 87-89° C. IR (KBr) $v_{max}$ 3437 (br), 3042, 2962, 2931, 2878, 1709, 1631 cm$^{-1}$. $^1$H NMR (CDCl$_3$) δ 5.51 (d, J=6.5 Hz, 1H), 5.39 (d, J=6.1 Hz, 1H), 5.30 (t, J=7.0 Hz, 1H), 4.14 (s, 2H), 2.77 (dt, J=5.8, 14.5 Hz, 1H), 2.34 (ddd, J=3.3, 4.4, 14.8, 1H), 2.28 (ddd, J=3.2, 5.7. 13.3 Hz, 1H), 2.25-1.90 (m, 6H), 1.80 (d, J=0.8 Hz, 3H), 1.76 (dt, J=4.4, 13.8 Hz, 1H), 1.68-1.28 (m, 10H), 1.20 (s, 3H), 1.13 (s, 3H), 1.09 (s, 3H), 0.91 (d, J=6.4 Hz, 3H), 0.87 (s, 3H), 0.59 (s, 3H). $^{13}$C{$^1$H} (CDCl$_3$) δ 216.8, 144.5, 142.9, 133.9, 129.1, 119.9, 117.3, 61.7, 50.8, 50.7, 50.3, 47.5, 43.7, 37.8, 37.2, 36.56, 36.60, 36.0, 34.8, 31.4, 27.9, 25.4, 25.3, 24.5, 23.7, 22.4, 22.0, 21.2, 18.4, 15.7. HRMS calcd for C$_{30}$H$_{47}$O$_2$ (M+H)$^+$ 439.3571. found 439.3585.

AD-mix. Alcohol 12Z (0.0138 g, 0.0325 mmol, 1.0 equiv) was dissolved in t-BuOH (0.33 mL) and water (0.33 mL). To this solution AD-mix-α (0.091 g, 2.8 g/mmol) was added followed by methanesulfonamide (0.0062 g, 0.065 mmol, 2.0 equiv). This solution was allowed to stir for 6 h at 25° C. Upon completion, an aqueous solution of sodium sulfite (5 mL) was added, and the quenched reaction mixture was allowed to stir for 1 h. The mixture was then diluted with ethyl acetate (5 mL), the phases separated, and the aqueous layer was then washed with ethyl acetate (4×5 mL). The combined organic layers were then washed with a saturated brine solution (20 mL), dried over MgSO$_4$, vacuum filtered through a pad of Celite, and the resulting filtrate was evaporated to dryness using a rotary evaporator. The solid was then purified using silica gel chromatography (pre-absorbed on silica gel, step gradient of 3:1 hexane/EtOAc followed by 100% MeOH) to afford 1 as a pure white crystalline solid (0.0114 g, 76% yield). The other isomeric triols were made by an analogous procedure to afford 13 (0.0100 g, 56% yield from 12Z with AD-mix-β), 14 (0.0137 g, 64% yield 12Z with AD-mix-α), 15 (0.0169 g, 76% yield from 12E with AD-mix-β).

(10S,13R,14R,17R)-4,4,10,13,14-Pentamethyl-17-((2R, 5S,6R)-5,6,7-trihydroxy-6-methylheptan-2-yl)-4,5,6,10,12, 13,14,15,16,17-decahydro-1H-cyclopenta[a]phenanthren-3 (2H)-one (Ganodermanontriol, 1): mp 145-147° C. [α]$^D_{23}$+ 33.6°. IR (KBr) $v_{max}$ 3343 (br), 3020, 2958, 2933, 2882, 1706, 1150, 1112, 1048, 812 cm$^{-1}$. $^1$H NMR (CDCl$_3$) δ 5.51 (br d, J=6.5 Hz, 1H), 5.38 (br d, J=6.2 Hz, 1H), 4.86 (br s, 2H), 3.83 (d, J=11.2 Hz, 1H), 3.49 (d, J=11.3 Hz, 1H), 3.45 (br d, 1H), 2.77 (dt, J=5.7, 14.6 Hz, 1H), 2.34 (m, 1H), 2.30-1.96 (m, 7H), 1.85-1.30 (m, 11H), 1.20 (s, 3H), 1.12 (s, 3H), 1.11 (s, 3H), 1.08 (s, 3H), 0.92 (d, J=6.4 Hz, 3H), 0.88 (s, 3H), 0.59 (s, 3H). 13C{1H} (CDCl$_3$) δ 216.9, 144.5, 142.8, 119.9, 117.2, 79.3, 74.0, 67.6, 51.0, 50.7, 50.3, 47.5, 43.8, 43.4, 37.8, 37.2, 36.6, 36.5, 34.8, 33.5, 31.4, 28.9, 27.9, 25.4, 25.3, 23.7, 22.0, 21.0, 18.6, 15.7. HRMS calcd for C$_{30}$H$_{49}$O$_4$ (M+H)$^+$, 473.3625. found 473.3641.

Literature Data: [α]$^D_{23}$+35.4°. $^1$H NMR (CDCl$_3$) δ 5.51 (dd, J=2.0, 6.1 Hz, 1H), 5.39 (dd, J=1.5, 5.0 Hz, 1H), 3.84 (d, J=11.3 Hz, 1H), 3.48 (m, 3H), 3.48 (d, J=11.3 Hz, 1H), 2.80 (m, 1H), 1.21 (s, 3H), 1.20 (s, 3H), 1.11 (s, 3H), 1.09 (s, 3H), 0.92 (d, J=6.1 Hz, 3H), 0.88 (s, 3H), 0.58 (s, 3H). 13C{1H} (CDCl$_3$) δ 217.00 (s), 144.43 (s), 142.77 (s), 119.87 (d), 117.22 (d), 79.10 (d), 74.07 (s), 67.59 (t), 50.96 (d), 50.66 (s), 50.29 (d), 47.47 (s), 43.67 (s), 37.76 (t), 37.17 (s), 36.55 (d), 36.55 (t), 34.84 (t), 33.53 (t), 31.45 (t), 28.83 (t), 27.87 (t), 25.42 (q), 25.42 (q), 25.42 (q), 23.61 (t), 22.04 (q), 20.88 (q), 18.64 (q), 15.73 (q).

(10S,13R,14R,17R)-4,4,10,13,14-Pentamethyl-17-((2R, 5R,6S)-5,6,7-trihydroxy-6-methylheptan-2-yl)-4,5,6,10,12, 13,14,15,16,17-decahydro-1H-cyclopenta[a]phenanthren-3 (2H)-one (13): mp 142-145° C. $[\alpha]^D_{23}$+36.3 (c=0.60, CHCl$_3$). IR (KBr) $\nu_{max}$ 3418 (br), 3040, 2964, 2927, 2881, 1700 cm$^{-1}$. $^1$H NMR (CDCl$_3$) δ 5.51 (d, J=6.7 Hz, 1H), 5.39 (d, J=6.3 Hz, 1H), 4.76 (br s, 1H), 3.84 (d, J=11.0 Hz, 1H), 3.50 (m, 2H), 2.80 (dt, J=5.8, 14.6 Hz, 1H), 2.50 (br m, 2H), 2.34 (m, 1H), 2.31-1.98 (m, 6H), 1.76 (dt, J=4.5, 14.0 Hz, 1H), 1.70-1.22 (m, 10H), 1.20 (s, 3H), 1.13 (s, 3H), 1.11 (s, 3H), 1.09 (s, 3H), 0.91 (d, J=6.4 Hz, 3H), 0.88 (s, 3H), 0.60 (s, 3H). $^{13}$C{$^1$H} (CDCl$_3$) δ 216.9, 144.5, 142.8, 119.9, 117.2, 77.2, 74.1, 69.3, 50.9, 50.7, 50.3, 47.5, 43.7, 37.8, 37.2, 36.6, 36.5, 34.8, 32.8, 31.4, 28.3, 27.9, 25.4, 25.3, 23.7, 22.7, 22.5, 22.0, 19.6, 18.6, 15.7. HRMS calcd for C$_{30}$H$_{49}$O$_4$ (M+H)$^+$ 473.3625. found 473.3619.

(10S,13R,14R,17R)-4,4,10,13,14-Pentamethyl-17-((2R, 5S,6S)-5,6,7-trihydroxy-6-methylheptan-2-yl)-4,5,6,10,12, 13,14,15,16,17-decahydro-1H-cyclopenta[a]phenanthren-3 (2H)-one (14): mp 139-141° C. $[\alpha]^D_{23}$+34.3 (c=0.87, CHCl$_3$). IR (KBr) $\nu_{max}$ 3477 (br), 3024, 2969, 2872, 1699 cm$^{-1}$. $^1$H NMR (CDCl$_3$) δ 5.51 (d, J=6.8 Hz, 1H), 5.38 (d, J=6.1 Hz, 1H), 3.65 (d, J=11.1 Hz, 1H), 3.55 (m, 1H), 3.49 (d, J=11.2 Hz, 1H), 2.78 (dt, J=5.7, 14.5 Hz, 1H), 2.34 (m, 1H), 2.30-1.96 (m, 7H), 1.76 (dt, J=4.3, 13.2 Hz, 1H), 1.68-1.2 (9H), 1.19 (s, 3H), 1.12 (s, 3H), 1.10 (s, 3H), 1.09 (s, 3H), 0.91 (d, J=6.5 Hz, 3H), 0.87 (s, 3H), 0.59 (s, 3H). 13C{1H} (CDCl$_3$) δ 216.8, 144.5, 142.8, 119.9, 117.2, 78.5, 73.9, 67.6, 51.0, 50.7, 50.3, 47.5, 43.7, 37.4, 37.2, 36.6, 34.8, 33.1, 31.4, 28.5, 27.9, 25.4, 25.3, 23.6, 22.0, 21.0, 18.3, 15.7. HRMS calcd for C$_{30}$H$_{49}$O$_4$ (M+H)$_+$ 473.3625. found 473.3616.

(10S,13R,14R,17R)-4,4,10,13,14-Pentamethyl-17-((2R, 5R,6R)-5,6,7-trihydroxy-6-methylheptan-2-yl)-4,5,6,10,12, 13,14,15,16,17-decahydro-1H-cyclopenta[a]phenanthren-3 (2H)-one (15): mp 134-135° C. $[\alpha]^D_{23}$+25.1 (c=0.42, CHCl$_3$). IR (KBr) $\nu_{max}$ 3335, 3018, 2964, 2924, 2883, 1707 cm$^{-1}$. $^1$H NMR (CDCl$_3$) δ 5.50 (d, J=6.9 Hz, 1H), 5.38 (d, J=6.5 Hz, 1H), 4.86 (br s, 1H), 3.64 (d, J=11.2 Hz, 1H), 3.61 (m, 1H), 3.52 (d, J=11.2 Hz, 1H), 2.77 (dt, J=5.7, 14.6 Hz, 1H), 2.34 (ddd, J=3.2, 4.4, 14.8 Hz, 1H), 2.21-1.97 (m, 6H), 1.75 (dt, J=4.5 Hz, 13.7 Hz, 1H), 1.66-1.23 (m, 10H), 1.20 (s, 3H), 1.12 (s, 3H), 1.09 (s, 3H), 1.08 (s, 3H), 0.91 (d, J=6.4 Hz, 3H), 0.88 (s, 3H), 0.59 (s, 3H). 13C{1H} (CDCl$_3$) δ 216.9, 144.5, 142.8, 119.9, 117.2, 76.2, 74.1, 69.4, 51.0, 50.7, 50.3, 47.5, 43.7, 43.4, 37.8, 37.2, 36.6, 34.8, 32.4, 31.4, 28.0, 27.9, 25.4, 25.3, 23.6, 22.0, 19.6, 18.3, 15.7. HRMS calcd for C$_{30}$H$_{49}$O$_4$ (M+H)$^+$ 473.3625. found 473.3615. Reproducible proton shifts were found in DMSO-d6 for the hydroxyl proton on C-24 of purified triols (1, δ 4.33; 13, δ 4.25; 14, δ 4.11; and 15, δ 4.05; all doublets, J=6.4±0.4 Hz). These signals were integrated with a relaxation delay of 2 seconds to determine the de for the asymmetric dihydroxylation reactions.

Cell culture: The human breast cancer cell lines MCF-7 and MDA-MB-231, obtained from ATCC (Manassas, Va.), were cultivated in Dulbecco's modified Eagle's medium (DMEM) containing penicillin (50 U/ml), streptomycin (50 U/ml), and 10% fetal bovine serum (FBS). Media and supplements were from Invitrogen (Grand Island, N.Y.).

Cell proliferation assay: Ganodermanontriol, 13, 14, and 15 (isomers) were dissolved in DMSO (Sigma; St. Louis, Mo.) at a concentration of 10 mM and stored at 4° C. Dulbecco's phosphate buffered saline (DPBS) was purchased from Cambrex Bio Science Walkersville, Inc. (Walkersville, Md.). Cell proliferation was determined by the tetrazolium salt method (MTT method), according to the manufacturer's instructions (Promega, Madison, Wis.). Briefly, MCF-7 and MDA-MB-231 cells (2.5×10$^3$/well) were cultured in a 96-well plate and treated with ganodermanontriol, 13, 14 and 15 (0-100 μg/ml) for 24, 48, and 72 hrs. At the end of the incubation period, the cells were harvested and absorption was determined with an ELISA plate reader at 570 nm. Data points represent mean±SD in triplicate determinations repeated at least twice. IC$_{50}$ values were determined by using SigmaPlot (Systat Software Inc, San Jose, Calif.).

What is claimed is:

1. A process for preparing a compound of formula (II)

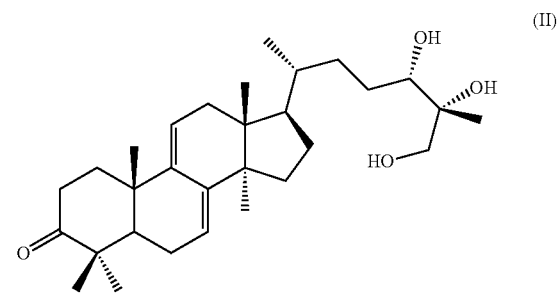

(II)

or a pharmaceutically acceptable salt thereof; the process comprising the steps:

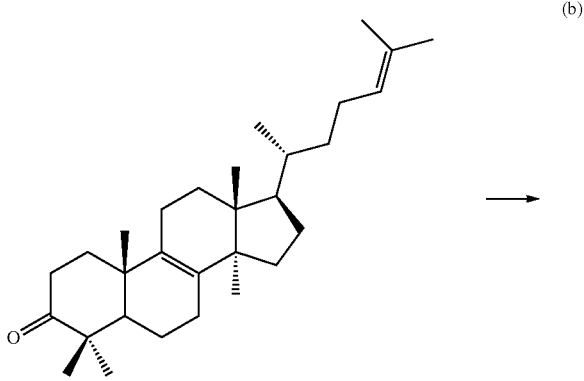

(b)

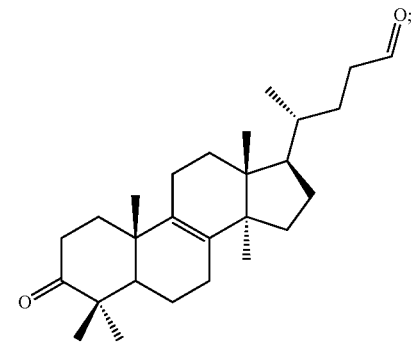

37
-continued
(c)
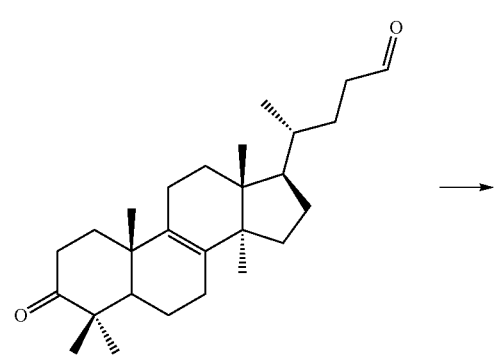
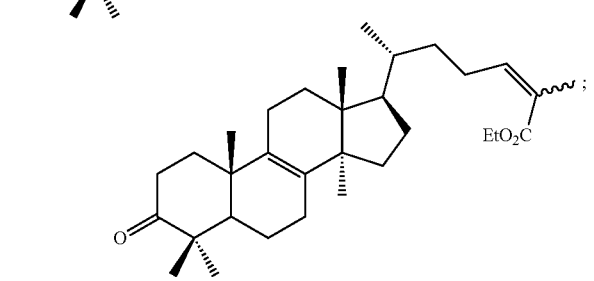
(e)
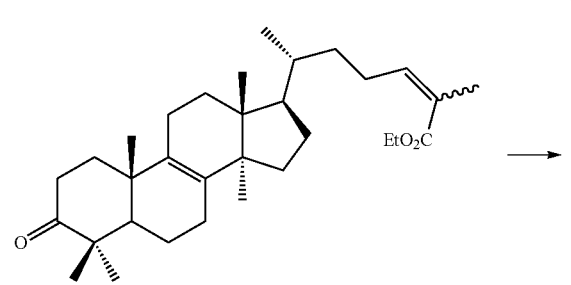
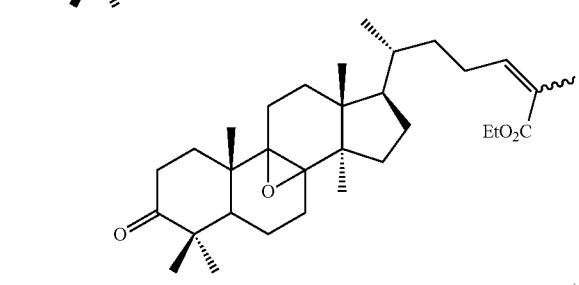
(f)
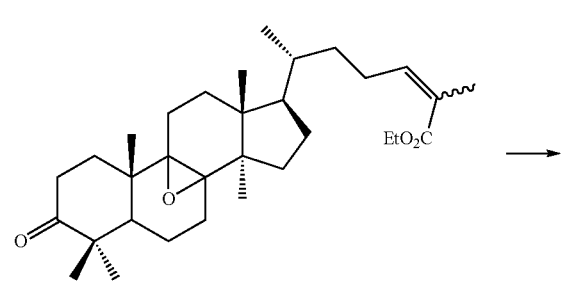
38
-continued
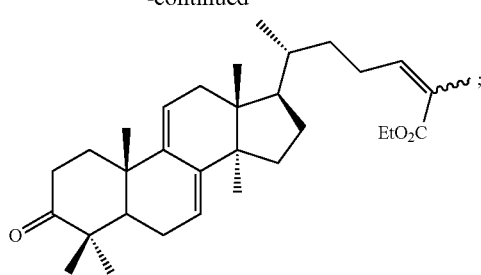
(d)
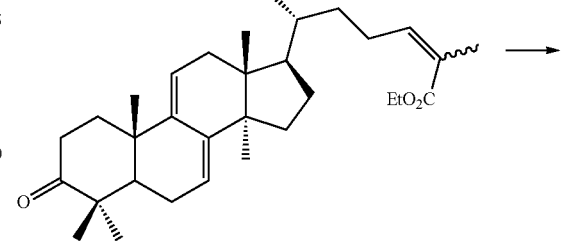
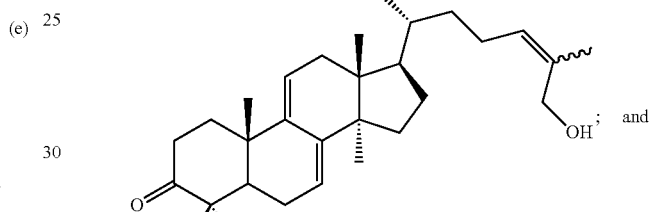
; and
(a)
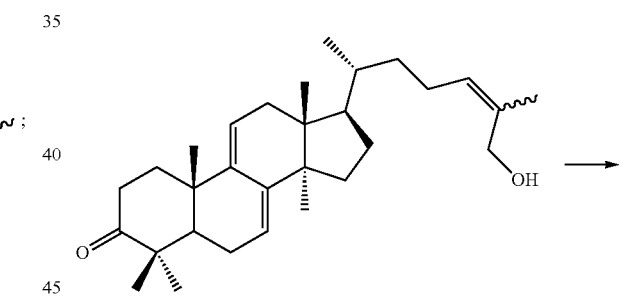
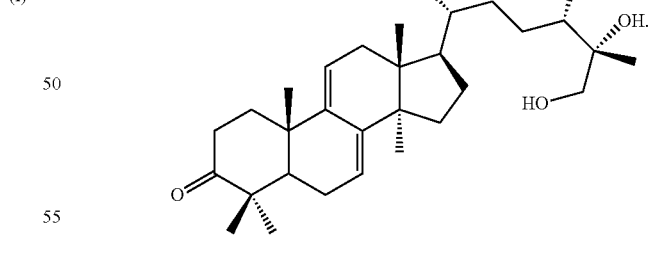
* * * * *